US012562251B1

(12) United States Patent
Hinkel et al.

(10) Patent No.: US 12,562,251 B1
(45) Date of Patent: Feb. 24, 2026

(54) COMPUTING ARCHITECTURE FOR ASSURING THE PROVENANCE OF MEDICATION THERAPY RELATED PARAMETERS, AND RELATED SYSTEMS, METHODS AND DEVICES

(71) Applicant: Bigfoot Biomedical, Inc., Milpitas, CA (US)

(72) Inventors: Cameron Hinkel, San Jose, CA (US); Kevin Lee, Milpitas, CA (US); Bryan Mazlish, Palo Alto, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 0 days.

(21) Appl. No.: 16/407,900

(22) Filed: May 9, 2019

Related U.S. Application Data

(60) Provisional application No. 62/669,250, filed on May 9, 2018.

(51) Int. Cl.
 *G16H 20/17* (2018.01)
 *A61B 5/00* (2006.01)
 (Continued)

(52) U.S. Cl.
 CPC ......... *G16H 20/17* (2018.01); *A61B 5/14532* (2013.01); *A61B 5/4839* (2013.01);
 (Continued)

(58) Field of Classification Search
 CPC .................................................. G16H 20/17
 See application file for complete search history.

(56) References Cited

U.S. PATENT DOCUMENTS 303,013 A   8/1884 Horton
445,545 A   2/1891 Crane
 (Continued)

FOREIGN PATENT DOCUMENTS

AU   2015200834 A1   3/2015
AU   2015301146 A1   3/2017
 (Continued)

OTHER PUBLICATIONS

US 5,954,699 A, 09/1999, Jost et al. (withdrawn)
 (Continued)

*Primary Examiner* — Robert A Sorey
*Assistant Examiner* — Kristine K Rapillo
(74) *Attorney, Agent, or Firm* — TraskBritt

(57) ABSTRACT

A mobile computing device for providing medication therapy recommendations includes a secure execution environment having one or more services executing therein. One service of the one or more services is configured to establish a secure user interaction process at the mobile computing device. The mobile computing device includes a normal execution environment having a medication therapy application executing therein. The medication therapy application is configured to determine at least one medication delivery instruction, request confirmation of the delivery instruction using the secure user interaction process, and provide certified medication delivery instructions to a communications interface configured for communication with a medication delivery unit responsive to a confirmation result. The confirmation result is received, at least in part, responsive to the secure user interaction process.

20 Claims, 20 Drawing Sheets

(51) Int. Cl.

| | |
|---|---|
| *A61B 5/145* | (2006.01) |
| *A61M 5/142* | (2006.01) |
| *G06F 3/0482* | (2013.01) |
| *G06F 21/44* | (2013.01) |
| *G16H 40/67* | (2018.01) |

(52) U.S. Cl.
CPC .......... *A61M 5/142* (2013.01); *G06F 3/0482* (2013.01); *G06F 21/44* (2013.01); *G16H 40/67* (2018.01)

(56) References Cited

U.S. PATENT DOCUMENTS

| | | | |
|---|---|---|---|
| 588,583 | A | 8/1897 | Lade |
| 1,441,508 | A | 1/1923 | Marius et al. |
| 2,283,925 | A | 5/1942 | Harvey |
| 2,797,149 | A | 6/1957 | Skeggs |
| 2,886,529 | A | 5/1959 | Guillaud |
| 3,413,573 | A | 11/1968 | Nathanson et al. |
| 3,574,114 | A | 4/1971 | Monforte |
| 3,614,554 | A | 10/1971 | Shield et al. |
| 3,631,847 | A | 1/1972 | Hobbs |
| 3,634,039 | A | 1/1972 | Brondy |
| 3,812,843 | A | 5/1974 | Wootten et al. |
| 3,841,328 | A | 10/1974 | Jensen |
| 3,885,662 | A | 5/1975 | Schaefer |
| 3,963,380 | A | 6/1976 | Thomas et al. |
| 3,983,077 | A | 9/1976 | Fuller et al. |
| 4,055,175 | A | 10/1977 | Clemens et al. |
| 4,108,177 | A | 8/1978 | Pistor |
| 4,146,029 | A | 3/1979 | Ellinwood, Jr. |
| 4,151,845 | A | 5/1979 | Clemens |
| 4,245,634 | A | 1/1981 | Albisser et al. |
| 4,268,150 | A | 5/1981 | Chen |
| 4,295,176 | A | 10/1981 | Wittwer |
| 4,313,439 | A | 2/1982 | Babb et al. |
| 4,368,980 | A | 1/1983 | Aldred et al. |
| 4,373,527 | A | 2/1983 | Fischell |
| 4,400,683 | A | 8/1983 | Eda et al. |
| 4,403,984 | A | 9/1983 | Ash et al. |
| 4,424,720 | A | 1/1984 | Bucchianeri |
| 4,435,173 | A | 3/1984 | Siposs et al. |
| 4,464,170 | A | 8/1984 | Clemens et al. |
| 4,469,481 | A | 9/1984 | Kobayashi |
| 4,475,901 | A | 10/1984 | Kraegen et al. |
| 4,498,843 | A | 2/1985 | Schneider et al. |
| 4,507,115 | A | 3/1985 | Kambara et al. |
| 4,523,170 | A | 6/1985 | Huth, III |
| 4,526,568 | A | 7/1985 | Clemens et al. |
| 4,526,569 | A | 7/1985 | Bernardi |
| 4,529,401 | A | 7/1985 | Leslie et al. |
| 4,551,134 | A | 11/1985 | Slavik et al. |
| 4,559,033 | A | 12/1985 | Stephen et al. |
| 4,559,037 | A | 12/1985 | Franetzki et al. |
| 4,562,751 | A | 1/1986 | Nason et al. |
| 4,573,968 | A | 3/1986 | Parker |
| 4,585,439 | A | 4/1986 | Michel |
| 4,601,707 | A | 7/1986 | Albisser et al. |
| 4,624,661 | A | 11/1986 | Arimond |
| 4,633,878 | A | 1/1987 | Bombardieri |
| 4,634,427 | A | 1/1987 | Hannula et al. |
| 4,646,038 | A | 2/1987 | Wanat |
| 4,657,529 | A | 4/1987 | Prince et al. |
| 4,678,408 | A | 7/1987 | Nason et al. |
| 4,684,368 | A | 8/1987 | Kenyon |
| 4,685,903 | A | 8/1987 | Cable et al. |
| 4,731,726 | A | 3/1988 | Allen, III |
| 4,743,243 | A | 5/1988 | Vaillancourt |
| 4,755,169 | A | 7/1988 | Sarnoff et al. |
| 4,755,173 | A | 7/1988 | Konopka et al. |
| 4,759,120 | A | 7/1988 | Bernstein |
| 4,781,688 | A | 11/1988 | Thoma et al. |
| 4,781,693 | A | 11/1988 | Martinez et al. |
| 4,808,161 | A | 2/1989 | Kamen |
| 4,854,170 | A | 8/1989 | Brimhall et al. |
| 4,859,492 | A | 8/1989 | Rogers et al. |
| 4,880,770 | A | 11/1989 | Mir et al. |
| 4,886,499 | A | 12/1989 | Cirelli et al. |
| 4,898,578 | A | 2/1990 | Rubalcaba, Jr. |
| 4,898,579 | A | 2/1990 | Groshong et al. |
| 4,900,292 | A | 2/1990 | Berry et al. |
| 4,919,596 | A | 4/1990 | Slate et al. |
| 4,925,444 | A | 5/1990 | Orkin et al. |
| 4,940,527 | A | 7/1990 | Kazlauskas et al. |
| 4,944,659 | A | 7/1990 | Labbe et al. |
| 4,967,201 | A | 10/1990 | Rich, III |
| 4,969,874 | A | 11/1990 | Michel et al. |
| 4,975,581 | A | 12/1990 | Robinson et al. |
| 4,976,720 | A | 12/1990 | Machold et al. |
| 4,981,140 | A | 1/1991 | Wyatt |
| 4,994,047 | A | 2/1991 | Walker et al. |
| 5,007,286 | A | 4/1991 | Malcolm et al. |
| 5,007,458 | A | 4/1991 | Marcus et al. |
| 5,061,424 | A | 10/1991 | Karimi et al. |
| 5,062,841 | A | 11/1991 | Siegel |
| 5,084,749 | A | 1/1992 | Losee et al. |
| 5,097,834 | A | 3/1992 | Skrabal |
| 5,102,406 | A | 4/1992 | Arnold |
| 5,109,850 | A | 5/1992 | Blanco et al. |
| 5,125,415 | A | 6/1992 | Bell |
| 5,130,675 | A | 7/1992 | Sugawara |
| 5,134,079 | A | 7/1992 | Cusack et al. |
| 5,139,999 | A | 8/1992 | Gordon et al. |
| 5,153,827 | A | 10/1992 | Coutre et al. |
| 5,154,973 | A | 10/1992 | Imagawa et al. |
| 5,165,406 | A | 11/1992 | Wong |
| 5,176,662 | A | 1/1993 | Bartholomew et al. |
| 5,178,609 | A | 1/1993 | Ishikawa |
| 5,189,609 | A | 2/1993 | Tivig et al. |
| 5,198,824 | A | 3/1993 | Poradish |
| 5,205,819 | A | 4/1993 | Ross et al. |
| 5,207,642 | A | 5/1993 | Orkin et al. |
| 5,213,483 | A | 5/1993 | Flaherty et al. |
| 5,217,754 | A | 6/1993 | Santiago-Aviles et al. |
| 5,219,377 | A | 6/1993 | Poradish |
| 5,232,439 | A | 8/1993 | Campbell et al. |
| 5,237,993 | A | 8/1993 | Skrabal |
| 5,244,463 | A | 9/1993 | Cordner et al. |
| 5,254,096 | A | 10/1993 | Rondelet et al. |
| 5,257,980 | A | 11/1993 | Van et al. |
| 5,261,882 | A | 11/1993 | Sealfon |
| 5,263,198 | A | 11/1993 | Geddes et al. |
| 5,272,485 | A | 12/1993 | Mason et al. |
| 5,273,517 | A | 12/1993 | Barone et al. |
| 5,281,202 | A | 1/1994 | Weber et al. |
| 5,281,808 | A | 1/1994 | Kunkel |
| 5,299,571 | A | 4/1994 | Mastrototaro |
| 5,308,982 | A | 5/1994 | Ivaldi et al. |
| 5,342,298 | A | 8/1994 | Michaels et al. |
| 5,346,476 | A | 9/1994 | Elson |
| 5,364,342 | A | 11/1994 | Beuchat et al. |
| 5,377,674 | A | 1/1995 | Kuestner |
| 5,380,665 | A | 1/1995 | Cusack et al. |
| 5,385,539 | A | 1/1995 | Maynard |
| 5,389,078 | A | 2/1995 | Zalesky et al. |
| 5,403,797 | A | 4/1995 | Ohtani et al. |
| 5,411,889 | A | 5/1995 | Hoots et al. |
| 5,421,812 | A | 6/1995 | Langley et al. |
| 5,427,988 | A | 6/1995 | Sengupta et al. |
| 5,433,710 | A | 7/1995 | Vanantwerp et al. |
| 5,456,945 | A | 10/1995 | Mcmillan et al. |
| 5,468,727 | A | 11/1995 | Phillips et al. |
| 5,478,610 | A | 12/1995 | Desu et al. |
| 5,505,709 | A | 4/1996 | Funderburk et al. |
| 5,505,828 | A | 4/1996 | Wong et al. |
| 5,507,288 | A | 4/1996 | Boecker et al. |
| 5,513,382 | A | 4/1996 | Agahi-Kesheh et al. |
| 5,533,389 | A | 7/1996 | Kamen et al. |
| 5,535,445 | A | 7/1996 | Gunton |
| 5,540,772 | A | 7/1996 | Mcmillan et al. |
| 5,543,773 | A | 8/1996 | Evans et al. |
| 5,558,640 | A | 9/1996 | Pfeiler et al. |
| 5,569,186 | A | 10/1996 | Lord et al. |
| 5,582,593 | A | 12/1996 | Hultman |

(56) References Cited

U.S. PATENT DOCUMENTS

| | | | |
|---|---|---|---|
| 5,584,053 | A | 12/1996 | Kommrusch et al. |
| 5,584,813 | A | 12/1996 | Livingston et al. |
| 5,590,387 | A | 12/1996 | Schmidt et al. |
| 5,609,572 | A | 3/1997 | Lang |
| 5,614,252 | A | 3/1997 | Mcmillan et al. |
| 5,625,365 | A | 4/1997 | Tom et al. |
| 5,635,433 | A | 6/1997 | Sengupta |
| 5,637,095 | A | 6/1997 | Nason et al. |
| 5,665,065 | A | 9/1997 | Colman et al. |
| 5,665,070 | A | 9/1997 | Mcphee |
| 5,678,539 | A | 10/1997 | Schubert et al. |
| 5,685,844 | A | 11/1997 | Marttila |
| 5,685,859 | A | 11/1997 | Kornerup |
| 5,693,018 | A | 12/1997 | Kriesel et al. |
| 5,697,899 | A | 12/1997 | Hillman et al. |
| 5,700,695 | A | 12/1997 | Yassinzadeh et al. |
| 5,703,364 | A | 12/1997 | Rosenthal |
| 5,707,459 | A | 1/1998 | Itoyama et al. |
| 5,707,715 | A | 1/1998 | Derochemont et al. |
| 5,713,875 | A | 2/1998 | Tanner, II |
| 5,714,123 | A | 2/1998 | Sohrab |
| 5,716,343 | A | 2/1998 | Kriesel et al. |
| 5,722,397 | A | 3/1998 | Eppstein |
| 5,741,228 | A | 4/1998 | Lambrecht et al. |
| 5,746,217 | A | 5/1998 | Erickson et al. |
| 5,747,350 | A | 5/1998 | Sattler |
| 5,747,870 | A | 5/1998 | Pedder |
| 5,748,827 | A | 5/1998 | Holl et al. |
| 5,755,682 | A | 5/1998 | Knudson et al. |
| 5,758,643 | A | 6/1998 | Wong et al. |
| 5,759,923 | A | 6/1998 | Mcmillan et al. |
| 5,764,189 | A | 6/1998 | Lohninger |
| 5,771,567 | A | 6/1998 | Pierce et al. |
| 5,776,103 | A | 7/1998 | Kriesel et al. |
| 5,779,676 | A | 7/1998 | Kriesel et al. |
| 5,785,688 | A | 7/1998 | Joshi et al. |
| 5,797,881 | A | 8/1998 | Gadot |
| 5,800,397 | A | 9/1998 | Wilson et al. |
| 5,800,405 | A | 9/1998 | Mcphee |
| 5,800,420 | A | 9/1998 | Gross et al. |
| 5,801,057 | A | 9/1998 | Smart et al. |
| 5,804,048 | A | 9/1998 | Wong et al. |
| 5,807,075 | A | 9/1998 | Jacobsen et al. |
| 5,817,007 | A | 10/1998 | Fodgaard et al. |
| 5,820,622 | A | 10/1998 | Gross et al. |
| 5,823,951 | A | 10/1998 | Messerschmidt |
| 5,839,467 | A | 11/1998 | Saaski et al. |
| 5,840,020 | A | 11/1998 | Heinonen et al. |
| D403,313 | S | 12/1998 | Peppel |
| 5,848,991 | A | 12/1998 | Gross et al. |
| 5,851,197 | A | 12/1998 | Marano et al. |
| 5,854,608 | A | 12/1998 | Leisten |
| 5,858,005 | A | 1/1999 | Kriesel |
| 5,858,239 | A | 1/1999 | Kenley et al. |
| 5,859,621 | A | 1/1999 | Leisten |
| 5,865,806 | A | 2/1999 | Howell |
| 5,871,470 | A | 2/1999 | Mcwha |
| 5,879,310 | A | 3/1999 | Sopp et al. |
| 5,889,459 | A | 3/1999 | Hattori et al. |
| 5,891,097 | A | 4/1999 | Saito et al. |
| 5,892,489 | A | 4/1999 | Kanba et al. |
| 5,897,530 | A | 4/1999 | Jackson |
| 5,902,253 | A | 5/1999 | Pfeiffer et al. |
| 5,903,421 | A | 5/1999 | Furutani et al. |
| 5,906,597 | A | 5/1999 | Mcphee |
| 5,911,716 | A | 6/1999 | Rake et al. |
| 5,919,167 | A | 7/1999 | Mulhauser et al. |
| 5,931,814 | A | 8/1999 | Alex et al. |
| 5,932,175 | A | 8/1999 | Knute et al. |
| 5,933,121 | A | 8/1999 | Rainhart et al. |
| 5,935,099 | A | 8/1999 | Peterson et al. |
| 5,945,963 | A | 8/1999 | Leisten |
| 5,947,911 | A | 9/1999 | Wong et al. |
| 5,957,890 | A | 9/1999 | Mann et al. |
| 5,961,492 | A | 10/1999 | Kriesel et al. |
| 5,965,848 | A | 10/1999 | Altschul et al. |
| 5,971,941 | A | 10/1999 | Simons et al. |
| 5,993,423 | A | 11/1999 | Choi |
| 5,997,501 | A | 12/1999 | Gross et al. |
| 6,005,151 | A | 12/1999 | Herrmann et al. |
| 6,017,318 | A | 1/2000 | Gauthier et al. |
| 6,019,747 | A | 2/2000 | Mcphee |
| 6,023,251 | A | 2/2000 | Koo et al. |
| 6,024,539 | A | 2/2000 | Blomquist |
| 6,027,826 | A | 2/2000 | Derochemont et al. |
| 6,028,568 | A | 2/2000 | Asakura et al. |
| 6,031,445 | A | 2/2000 | Marty et al. |
| 6,032,059 | A | 2/2000 | Henning et al. |
| 6,036,924 | A | 3/2000 | Simons et al. |
| 6,040,578 | A | 3/2000 | Malin et al. |
| 6,040,805 | A | 3/2000 | Huynh et al. |
| 6,046,707 | A | 4/2000 | Gaughan et al. |
| 6,049,727 | A | 4/2000 | Crothall |
| 6,050,978 | A | 4/2000 | Orr et al. |
| 6,052,040 | A | 4/2000 | Hino |
| 6,058,934 | A | 5/2000 | Sullivan |
| 6,066,103 | A | 5/2000 | Duchon et al. |
| 6,071,292 | A | 6/2000 | Makower et al. |
| 6,072,180 | A | 6/2000 | Kramer et al. |
| 6,077,055 | A | 6/2000 | Scott |
| 6,090,092 | A | 7/2000 | Fowles et al. |
| 6,101,406 | A | 8/2000 | Hacker et al. |
| 6,102,872 | A | 8/2000 | Doneen et al. |
| 6,111,544 | A | 8/2000 | Dakeya et al. |
| 6,115,673 | A | 9/2000 | Malin et al. |
| 6,123,827 | A | 9/2000 | Wong et al. |
| 6,124,134 | A | 9/2000 | Stark |
| 6,126,637 | A | 10/2000 | Kriesel et al. |
| 6,128,519 | A | 10/2000 | Say |
| 6,142,939 | A | 11/2000 | Eppstein et al. |
| 6,143,164 | A | 11/2000 | Heller et al. |
| 6,143,432 | A | 11/2000 | De et al. |
| 6,154,176 | A | 11/2000 | Fathy et al. |
| 6,157,041 | A | 12/2000 | Thomas et al. |
| 6,161,028 | A | 12/2000 | Braig et al. |
| 6,162,639 | A | 12/2000 | Douglas |
| 6,174,300 | B1 | 1/2001 | Kriesel et al. |
| 6,176,004 | B1 | 1/2001 | Rainhart et al. |
| 6,181,297 | B1 | 1/2001 | Leisten |
| 6,188,368 | B1 | 2/2001 | Koriyama et al. |
| 6,190,359 | B1 | 2/2001 | Heruth |
| 6,195,049 | B1 | 2/2001 | Kim et al. |
| 6,196,046 | B1 | 3/2001 | Braig et al. |
| 6,200,287 | B1 | 3/2001 | Keller et al. |
| 6,200,293 | B1 | 3/2001 | Kriesel et al. |
| 6,200,338 | B1 | 3/2001 | Solomon et al. |
| 6,204,203 | B1 | 3/2001 | Narwankar et al. |
| 6,208,843 | B1 | 3/2001 | Huang et al. |
| 6,214,629 | B1 | 4/2001 | Freitag et al. |
| 6,222,489 | B1 | 4/2001 | Tsuru et al. |
| 6,226,082 | B1 | 5/2001 | Roe |
| 6,244,776 | B1 | 6/2001 | Wiley |
| 6,261,065 | B1 | 7/2001 | Nayak et al. |
| 6,262,798 | B1 | 7/2001 | Shepherd et al. |
| 6,266,020 | B1 | 7/2001 | Chang |
| 6,270,455 | B1 | 8/2001 | Brown |
| 6,271,045 | B1 | 8/2001 | Douglas et al. |
| 6,280,381 | B1 | 8/2001 | Malin et al. |
| 6,285,448 | B1 | 9/2001 | Kuenstner |
| 6,300,894 | B1 | 10/2001 | Lynch et al. |
| 6,309,370 | B1 | 10/2001 | Haim et al. |
| 6,312,888 | B1 | 11/2001 | Wong et al. |
| 6,320,547 | B1 | 11/2001 | Fathy et al. |
| 6,323,549 | B1 | 11/2001 | Derochemont et al. |
| 6,334,851 | B1 | 1/2002 | Hayes et al. |
| 6,363,609 | B1 | 4/2002 | Pickren |
| 6,375,627 | B1 | 4/2002 | Mauze et al. |
| 6,375,638 | B2 | 4/2002 | Nason et al. |
| 6,379,301 | B1 | 4/2002 | Worthington et al. |
| 6,402,689 | B1 | 6/2002 | Scarantino et al. |
| 6,413,244 | B1 | 7/2002 | Bestetti et al. |
| 6,470,279 | B1 | 10/2002 | Samsoondar |
| 6,474,219 | B2 | 11/2002 | Klitmose et al. |
| 6,475,196 | B1 | 11/2002 | Vachon |

(56)  References Cited

U.S. PATENT DOCUMENTS

| | | | |
|---|---|---|---|
| 6,477,065 B2 | 11/2002 | Parks |
| 6,477,901 B1 | 11/2002 | Tadigadapa et al. |
| 6,484,044 B1 | 11/2002 | Lilienfeld-Toal |
| 6,485,461 B1 | 11/2002 | Mason et al. |
| 6,485,462 B1 | 11/2002 | Kriesel |
| 6,491,656 B1 | 12/2002 | Morris |
| 6,492,949 B1 | 12/2002 | Breglia et al. |
| 6,496,149 B1 | 12/2002 | Birnbaum et al. |
| 6,501,415 B1 | 12/2002 | Mana et al. |
| 6,512,937 B2 | 1/2003 | Blank et al. |
| 6,520,936 B1 | 2/2003 | Mann |
| 6,525,509 B1 | 2/2003 | Petersson et al. |
| 6,527,744 B1 | 3/2003 | Kriesel et al. |
| 6,528,809 B1 | 3/2003 | Thomas et al. |
| 6,537,249 B2 | 3/2003 | Kriesell et al. |
| 6,540,260 B1 | 4/2003 | Tan |
| 6,540,672 B1 | 4/2003 | Simonsen et al. |
| 6,541,820 B1 | 4/2003 | Bol |
| 6,544,212 B2 | 4/2003 | Galley et al. |
| 6,546,268 B1 | 4/2003 | Ishikawa et al. |
| 6,546,269 B1 | 4/2003 | Kurnik |
| 6,552,693 B1 | 4/2003 | Leisten |
| 6,553,841 B1 | 4/2003 | Blouch |
| 6,554,798 B1 | 4/2003 | Mann et al. |
| 6,556,850 B1 | 4/2003 | Braig et al. |
| D474,778 S | 5/2003 | Barnes |
| 6,558,351 B1 | 5/2003 | Steil et al. |
| 6,559,735 B1 | 5/2003 | Hoang et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,115 B1 | 5/2003 | Barker et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,583,699 B2 | 6/2003 | Yokoyama |
| 6,595,956 B1 | 7/2003 | Gross et al. |
| 6,611,419 B1 | 8/2003 | Chakravorty |
| 6,618,603 B2 | 9/2003 | Varalli et al. |
| 6,620,750 B2 | 9/2003 | Kim et al. |
| 6,633,772 B2 | 10/2003 | Ford et al. |
| 6,635,958 B2 | 10/2003 | Bates et al. |
| 6,639,556 B2 | 10/2003 | Baba |
| 6,642,908 B2 | 11/2003 | Pleva et al. |
| 6,645,142 B2 | 11/2003 | Braig et al. |
| 6,650,303 B2 | 11/2003 | Kim et al. |
| 6,653,091 B1 | 11/2003 | Dunn et al. |
| 6,656,158 B2 | 12/2003 | Mahoney et al. |
| 6,662,030 B2 | 12/2003 | Khalil et al. |
| 6,669,663 B1 | 12/2003 | Thompson |
| 6,670,497 B2 | 12/2003 | Tashino et al. |
| 6,678,542 B2 | 1/2004 | Braig et al. |
| 6,680,700 B2 | 1/2004 | Hilgers |
| 6,683,576 B2 | 1/2004 | Achim |
| 6,686,406 B2 | 2/2004 | Tomomatsu et al. |
| 6,690,336 B1 | 2/2004 | Leisten et al. |
| 6,697,605 B1 | 2/2004 | Atokawa et al. |
| 6,699,218 B2 | 3/2004 | Flaherty et al. |
| 6,699,221 B2 | 3/2004 | Vaillancourt |
| 6,718,189 B2 | 4/2004 | Rohrscheib et al. |
| 6,720,926 B2 | 4/2004 | Killen et al. |
| 6,721,582 B2 | 4/2004 | Trepagnier et al. |
| 6,723,072 B2 | 4/2004 | Flaherty et al. |
| 6,727,785 B2 | 4/2004 | Killen et al. |
| 6,728,560 B2 | 4/2004 | Kollias et al. |
| 6,731,244 B2 | 5/2004 | Killen et al. |
| 6,731,248 B2 | 5/2004 | Killen et al. |
| 6,733,890 B2 | 5/2004 | Imanaka et al. |
| 6,740,059 B2 | 5/2004 | Flaherty |
| 6,740,072 B2 | 5/2004 | Starkweather et al. |
| 6,741,148 B2 | 5/2004 | Killen et al. |
| 6,742,249 B2 | 6/2004 | Derochemont et al. |
| 6,743,744 B1 | 6/2004 | Kim et al. |
| 6,750,740 B2 | 6/2004 | Killen et al. |
| 6,750,820 B2 | 6/2004 | Killen et al. |
| 6,751,490 B2 | 6/2004 | Esenaliev et al. |
| 6,753,745 B2 | 6/2004 | Killen et al. |
| 6,753,814 B2 | 6/2004 | Killen et al. |
| 6,758,835 B2 | 7/2004 | Close et al. |
| 6,762,237 B2 | 7/2004 | Glatkowski et al. |
| 6,780,156 B2 | 8/2004 | Haueter et al. |
| 6,787,181 B2 | 9/2004 | Uchiyama et al. |
| 6,791,496 B1 | 9/2004 | Killen et al. |
| 6,810,290 B2 | 10/2004 | Lebel et al. |
| 6,826,031 B2 | 11/2004 | Nagai et al. |
| 6,830,623 B2 | 12/2004 | Hayashi et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,853,288 B2 | 2/2005 | Ahn et al. |
| 6,858,892 B2 | 2/2005 | Yamagata |
| 6,862,534 B2 | 3/2005 | Sterling et al. |
| 6,864,848 B2 | 3/2005 | Sievenpiper |
| 6,865,408 B1 | 3/2005 | Abbink et al. |
| 6,871,396 B2 | 3/2005 | Sugaya et al. |
| 6,878,871 B2 | 4/2005 | Scher et al. |
| 6,883,778 B1 | 4/2005 | Newton et al. |
| 6,890,291 B2 | 5/2005 | Robinson et al. |
| 6,905,989 B2 | 6/2005 | Ellis et al. |
| 6,906,674 B2 | 6/2005 | Mckinzie et al. |
| 6,914,566 B2 | 7/2005 | Beard |
| 6,919,119 B2 | 7/2005 | Kalkan et al. |
| 6,928,298 B2 | 8/2005 | Furutani et al. |
| 6,936,029 B2 | 8/2005 | Mann et al. |
| 6,943,430 B2 | 9/2005 | Kwon |
| 6,943,731 B2 | 9/2005 | Killen et al. |
| 6,949,081 B1 | 9/2005 | Chance |
| 6,958,809 B2 | 10/2005 | Sterling et al. |
| 6,963,259 B2 | 11/2005 | Killen et al. |
| 6,989,891 B2 | 1/2006 | Braig et al. |
| 6,990,366 B2 | 1/2006 | Say et al. |
| 7,002,436 B2 | 2/2006 | Ma et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis et al. |
| 7,047,637 B2 | 5/2006 | Derochemont et al. |
| 7,060,059 B2 | 6/2006 | Keith et al. |
| 7,060,350 B2 | 6/2006 | Takaya et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,116,949 B2 | 10/2006 | Irie et al. |
| 7,128,727 B2 | 10/2006 | Flaherty et al. |
| 7,137,694 B2 | 11/2006 | Ferran et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,160,272 B1 | 1/2007 | Eyal et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,230,316 B2 | 6/2007 | Yamazaki et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,291,782 B2 | 11/2007 | Sager et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |

(56)       References Cited

U.S. PATENT DOCUMENTS

| | | | |
|---|---|---|---|
| 7,404,796 B2 | 7/2008 | Ginsberg |
| 7,405,698 B2 | 7/2008 | De Rochemont |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van et al. |
| 7,500,949 B2 | 3/2009 | Gottlieb et al. |
| 7,509,156 B2 | 3/2009 | Flanders |
| D590,415 S | 4/2009 | Ball et al. |
| 7,522,124 B2 | 4/2009 | Smith et al. |
| 7,547,281 B2 | 6/2009 | Hayes et al. |
| 7,553,512 B2 | 6/2009 | Kodas et al. |
| 7,564,887 B2 | 7/2009 | Wang et al. |
| 7,569,030 B2 | 8/2009 | Lebel et al. |
| 7,595,623 B2 | 9/2009 | Bennett |
| 7,608,042 B2 | 10/2009 | Goldberger et al. |
| 7,651,845 B2 | 1/2010 | Doyle et al. |
| 7,652,901 B2 | 1/2010 | Kirchmeier et al. |
| 7,680,529 B2 | 3/2010 | Kroll |
| D614,634 S | 4/2010 | Nilsen |
| 7,714,794 B2 | 5/2010 | Tavassoli Hozouri |
| 7,734,323 B2 | 6/2010 | Blomquist et al. |
| 7,763,917 B2 | 7/2010 | De Rochemont |
| 7,766,829 B2 | 8/2010 | Sloan et al. |
| 7,771,391 B2 | 8/2010 | Carter |
| 7,785,258 B2 | 8/2010 | Braig et al. |
| 7,806,854 B2 | 10/2010 | Damiano et al. |
| 7,806,886 B2 | 10/2010 | Kanderian et al. |
| 7,812,774 B2 | 10/2010 | Friman et al. |
| 7,918,825 B2 | 4/2011 | O'Connor et al. |
| 7,946,985 B2 | 5/2011 | Mastrototaro et al. |
| D640,269 S | 6/2011 | Chen |
| 7,972,296 B2 | 7/2011 | Braig et al. |
| 8,066,805 B2 | 11/2011 | Zuercher et al. |
| 8,069,690 B2 | 12/2011 | Desantolo et al. |
| 8,114,489 B2 | 2/2012 | Nemat-Nasser et al. |
| 8,178,457 B2 | 5/2012 | De Rochemont |
| 8,193,873 B2 | 6/2012 | Kato et al. |
| 8,221,345 B2 | 7/2012 | Blomquist |
| 8,251,907 B2 | 8/2012 | Sterling et al. |
| 8,267,921 B2 | 9/2012 | Yodfat et al. |
| 8,350,657 B2 | 1/2013 | Derochemont |
| 8,354,294 B2 | 1/2013 | De et al. |
| D677,685 S | 3/2013 | Simmons et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| D688,686 S | 8/2013 | Rhee et al. |
| 8,547,239 B2 | 10/2013 | Peatfield et al. |
| D693,837 S | 11/2013 | Bouchier |
| 8,593,819 B2 | 11/2013 | De Rochemont |
| D695,757 S | 12/2013 | Ray et al. |
| 8,597,274 B2 | 12/2013 | Sloan et al. |
| 8,622,988 B2 | 1/2014 | Hayter |
| 8,715,839 B2 | 5/2014 | De Rochemont |
| D710,879 S | 8/2014 | Elston et al. |
| 8,810,394 B2 | 8/2014 | Kalpin |
| D714,822 S | 10/2014 | Capua et al. |
| D715,315 S | 10/2014 | Wood |
| D715,815 S | 10/2014 | Bortman et al. |
| D718,779 S | 12/2014 | Hang et al. |
| D720,366 S | 12/2014 | Hiltunen et al. |
| D720,765 S | 1/2015 | Xie et al. |
| 8,939,935 B2 | 1/2015 | O'Connor et al. |
| D726,760 S | 4/2015 | Yokota et al. |
| D727,928 S | 4/2015 | Allison et al. |
| D730,378 S | 5/2015 | Xiong et al. |
| D733,175 S | 6/2015 | Bae |
| 9,061,097 B2 | 6/2015 | Holt et al. |
| D734,356 S | 7/2015 | Xiong et al. |
| D736,811 S | 8/2015 | Teichner et al. |
| D737,305 S | 8/2015 | Scazafavo et al. |
| D737,831 S | 9/2015 | Lee |
| D737,832 S | 9/2015 | Lim et al. |
| D738,901 S | 9/2015 | Amin |
| D740,301 S | 10/2015 | Soegiono et al. |
| D740,308 S | 10/2015 | Kim et al. |
| D740,311 S | 10/2015 | Drozd et al. |
| D741,354 S | 10/2015 | Lee et al. |
| D741,359 S | 10/2015 | Ji-Hye et al. |
| 9,171,343 B1 | 10/2015 | Fischell et al. |
| D743,431 S | 11/2015 | Pal et al. |
| D743,991 S | 11/2015 | Pal et al. |
| 9,180,224 B2 | 11/2015 | Moseley et al. |
| 9,180,244 B2 | 11/2015 | Anderson et al. |
| 9,192,716 B2 | 11/2015 | Jugl et al. |
| D744,514 S | 12/2015 | Shin et al. |
| D744,517 S | 12/2015 | Pal et al. |
| D745,032 S | 12/2015 | Pal et al. |
| D745,034 S | 12/2015 | Pal et al. |
| D745,035 S | 12/2015 | Pal et al. |
| D746,827 S | 1/2016 | Jung et al. |
| D746,828 S | 1/2016 | Arai et al. |
| D747,352 S | 1/2016 | Lee et al. |
| 9,233,204 B2 | 1/2016 | Booth et al. |
| D749,097 S | 2/2016 | Zou et al. |
| D749,118 S | 2/2016 | Wang |
| D751,100 S | 3/2016 | Lindn et al. |
| D752,604 S | 3/2016 | Zhang |
| D753,134 S | 4/2016 | Vazquez |
| D754,718 S | 4/2016 | Zhou |
| D755,193 S | 5/2016 | Sun et al. |
| D755,799 S | 5/2016 | Finnis et al. |
| D755,820 S | 5/2016 | Wang |
| D756,387 S | 5/2016 | Chang et al. |
| D757,032 S | 5/2016 | Sabia et al. |
| D757,035 S | 5/2016 | Raskin et al. |
| D758,391 S | 6/2016 | Suarez |
| D758,422 S | 6/2016 | Zhao |
| D759,032 S | 6/2016 | Amin et al. |
| D759,078 S | 6/2016 | Iwamoto |
| D759,678 S | 6/2016 | Jung et al. |
| D759,687 S | 6/2016 | Chang et al. |
| D761,812 S | 7/2016 | Motamedi |
| D763,308 S | 8/2016 | Wang et al. |
| D763,868 S | 8/2016 | Lee et al. |
| D765,110 S | 8/2016 | Liang |
| D765,124 S | 8/2016 | Minks-Brown et al. |
| 9,402,950 B2 | 8/2016 | Dilanni et al. |
| D765,707 S | 9/2016 | Gomez |
| D766,286 S | 9/2016 | Lee et al. |
| D767,586 S | 9/2016 | Kwon et al. |
| D768,154 S | 10/2016 | Kim et al. |
| D768,188 S | 10/2016 | Li et al. |
| D768,660 S | 10/2016 | Wielgosz |
| D768,685 S | 10/2016 | Lee et al. |
| D769,315 S | 10/2016 | Scotti |
| D770,507 S | 11/2016 | Umezawa et al. |
| D770,515 S | 11/2016 | Cho et al. |
| D771,073 S | 11/2016 | Choi et al. |
| D771,076 S | 11/2016 | Butcher et al. |
| D771,690 S | 11/2016 | Yin et al. |
| D772,911 S | 11/2016 | Lee et al. |
| 9,486,571 B2 | 11/2016 | Rosinko |
| D773,531 S | 12/2016 | Toth et al. |
| D775,184 S | 12/2016 | Song et al. |
| D775,196 S | 12/2016 | Huang et al. |
| 9,520,649 B2 | 12/2016 | De Rochemont |
| D775,658 S | 1/2017 | Luo et al. |
| D776,126 S | 1/2017 | Lai et al. |
| D776,687 S | 1/2017 | Wick et al. |
| D777,191 S | 1/2017 | Polimeni |
| D777,758 S | 1/2017 | Kisselev et al. |
| 9,579,456 B2 | 2/2017 | Budiman et al. |
| D781,323 S | 3/2017 | Green et al. |
| D781,781 S | 3/2017 | Schimmoeller, Jr. |
| D781,877 S | 3/2017 | Ko et al. |
| D781,878 S | 3/2017 | Butcher et al. |
| D781,879 S | 3/2017 | Butcher et al. |
| D781,903 S | 3/2017 | Reichle et al. |
| D781,905 S | 3/2017 | Nakaguchi et al. |
| D782,506 S | 3/2017 | Kim et al. |

(56) References Cited

U.S. PATENT DOCUMENTS

| | | | |
|---|---|---|---|
| D783,672 S | 4/2017 | Rajasankar et al. |
| D785,010 S | 4/2017 | Bachman et al. |
| D785,656 S | 5/2017 | Bramer et al. |
| D786,278 S | 5/2017 | Motamedi |
| D786,898 S | 5/2017 | Hall |
| D788,126 S | 5/2017 | Evnin et al. |
| 9,656,017 B2 | 5/2017 | Greene |
| D788,621 S | 6/2017 | Shallice et al. |
| D788,652 S | 6/2017 | Mutsuro et al. |
| D789,402 S | 6/2017 | Dye et al. |
| D789,967 S | 6/2017 | Kaplan et al. |
| D789,982 S | 6/2017 | Christiana et al. |
| D790,560 S | 6/2017 | Inose et al. |
| D791,781 S | 7/2017 | Donarski et al. |
| D791,805 S | 7/2017 | Segars |
| D791,812 S | 7/2017 | Bistoni et al. |
| D793,412 S | 8/2017 | Chaudhri et al. |
| D795,886 S | 8/2017 | Ng et al. |
| D795,891 S | 8/2017 | Kohan et al. |
| D795,900 S | 8/2017 | Bischoff et al. |
| D795,906 S | 8/2017 | Butrick |
| D795,927 S | 8/2017 | Bischoff et al. |
| 9,743,224 B2 | 8/2017 | San et al. |
| D796,530 S | 9/2017 | Mcmillan et al. |
| D796,540 S | 9/2017 | Mclean et al. |
| D797,116 S | 9/2017 | Chapman et al. |
| D797,763 S | 9/2017 | Kim et al. |
| D797,774 S | 9/2017 | Park et al. |
| D797,797 S | 9/2017 | Gandhi et al. |
| D798,310 S | 9/2017 | Golden et al. |
| D798,311 S | 9/2017 | Golden et al. |
| D799,536 S | 10/2017 | Eder |
| D800,765 S | 10/2017 | Stoksik |
| D800,769 S | 10/2017 | Hennessy et al. |
| D801,383 S | 10/2017 | Park et al. |
| D802,011 S | 11/2017 | Friedman et al. |
| D802,088 S | 11/2017 | Bos et al. |
| D803,232 S | 11/2017 | Leigh et al. |
| D803,242 S | 11/2017 | Mizono et al. |
| D804,502 S | 12/2017 | Amini et al. |
| D805,525 S | 12/2017 | Dascola et al. |
| D806,716 S | 1/2018 | Pahwa et al. |
| D807,376 S | 1/2018 | Mizono et al. |
| D807,400 S | 1/2018 | Lagreca |
| D807,910 S | 1/2018 | Graham et al. |
| D807,918 S | 1/2018 | Cohen et al. |
| D807,919 S | 1/2018 | Cohen et al. |
| D808,423 S | 1/2018 | Jiang et al. |
| D808,974 S | 1/2018 | Chiappone et al. |
| D808,983 S | 1/2018 | Narinedhat et al. |
| 9,857,090 B2 | 1/2018 | Golden et al. |
| D810,116 S | 2/2018 | Mclean et al. |
| D810,771 S | 2/2018 | Gandhi et al. |
| 9,907,515 B2 | 3/2018 | Doyle et al. |
| D815,131 S | 4/2018 | Thompson et al. |
| D816,090 S | 4/2018 | Stonecipher et al. |
| D817,339 S | 5/2018 | Nanjappan et al. |
| D818,491 S | 5/2018 | Timmer et al. |
| D819,057 S | 5/2018 | Huang |
| D819,059 S | 5/2018 | Julia |
| 9,980,140 B1 | 5/2018 | Spencer et al. |
| 9,984,773 B2 | 5/2018 | Gondhalekar et al. |
| D820,311 S | 6/2018 | Cabrera et al. |
| D820,862 S | 6/2018 | Alfonzo et al. |
| D822,034 S | 7/2018 | Clymer et al. |
| D822,677 S | 7/2018 | Weaver et al. |
| D822,684 S | 7/2018 | Clausen-Stuck et al. |
| D822,692 S | 7/2018 | Loychik et al. |
| D823,862 S | 7/2018 | Chung et al. |
| D824,400 S | 7/2018 | Chang et al. |
| D824,951 S | 8/2018 | Kolbrener et al. |
| D826,956 S | 8/2018 | Pillalamarri et al. |
| D826,957 S | 8/2018 | Pillalamarri et al. |
| D828,381 S | 9/2018 | Lee et al. |
| D829,732 S | 10/2018 | Jeffrey et al. |
| D830,374 S | 10/2018 | Leonard et al. |
| D830,384 S | 10/2018 | Lepine et al. |
| D830,385 S | 10/2018 | Lepine et al. |
| D830,407 S | 10/2018 | Kisielius et al. |
| D831,033 S | 10/2018 | Leonard et al. |
| D833,469 S | 11/2018 | Coleman et al. |
| D834,601 S | 11/2018 | Felt |
| D835,132 S | 12/2018 | Ito et al. |
| D835,145 S | 12/2018 | Cashner et al. |
| D835,147 S | 12/2018 | Kisielius et al. |
| D835,651 S | 12/2018 | Bao |
| D835,666 S | 12/2018 | Saleh et al. |
| D836,123 S | 12/2018 | Pillalamarri et al. |
| D837,807 S | 1/2019 | Baber et al. |
| D838,731 S | 1/2019 | Pillalamarri et al. |
| D840,418 S | 2/2019 | Saad et al. |
| D840,419 S | 2/2019 | Saad et al. |
| D844,022 S | 3/2019 | Amin |
| D845,317 S | 4/2019 | Wellmeier et al. |
| 10,248,839 B2 | 4/2019 | Levy et al. |
| D848,459 S | 5/2019 | Li |
| D851,099 S | 6/2019 | Uppala et al. |
| D851,658 S | 6/2019 | Pillalamarri et al. |
| 10,335,464 B1 | 7/2019 | Michelich et al. |
| D865,795 S | 11/2019 | Koo |
| D872,746 S | 1/2020 | Laborde |
| D874,471 S | 2/2020 | Pillalamarri et al. |
| D875,114 S | 2/2020 | Clediere |
| 10,583,250 B2 | 3/2020 | Mazlish et al. |
| D880,498 S | 4/2020 | Shahidi et al. |
| D888,070 S | 6/2020 | Yusupov et al. |
| 10,737,024 B2 | 8/2020 | Schmid |
| D904,426 S | 12/2020 | Paul |
| D911,353 S | 2/2021 | Sanchez et al. |
| D914,031 S | 3/2021 | Ding et al. |
| D916,729 S | 4/2021 | Gabriel et al. |
| D916,870 S | 4/2021 | Hemsley |
| D916,878 S | 4/2021 | Kim et al. |
| 10,987,468 B2 | 4/2021 | Mazlish et al. |
| D918,261 S | 5/2021 | Ramamurthy et al. |
| D920,351 S | 5/2021 | Zhang |
| D923,033 S | 6/2021 | Smith et al. |
| D927,533 S | 8/2021 | Clymer |
| D938,447 S | 12/2021 | Holland |
| 11,197,964 B2 | 12/2021 | Sjolund et al. |
| 11,260,169 B2 | 3/2022 | Estes |
| D954,078 S | 6/2022 | Rahate et al. |
| 2001/0021803 A1 | 9/2001 | Blank et al. |
| 2001/0034023 A1 | 10/2001 | Stanton et al. |
| 2001/0034502 A1 | 10/2001 | Moberg et al. |
| 2001/0048969 A1 | 12/2001 | Constantino et al. |
| 2001/0051377 A1 | 12/2001 | Hammer et al. |
| 2001/0053895 A1 | 12/2001 | Vaillancourt |
| 2001/0056258 A1 | 12/2001 | Evans |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0047768 A1 | 4/2002 | Duffy |
| 2002/0070983 A1 | 6/2002 | Kozub et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2002/0173769 A1 | 11/2002 | Gray et al. |
| 2002/0190818 A1 | 12/2002 | Endou et al. |
| 2003/0023148 A1 | 1/2003 | Lorenz et al. |
| 2003/0023152 A1 | 1/2003 | Abbink et al. |
| 2003/0034124 A1 | 2/2003 | Sugaya et al. |
| 2003/0040715 A1 | 2/2003 | D'Antonio et al. |
| 2003/0050621 A1 | 3/2003 | Lebel et al. |
| 2003/0060692 A1 | 3/2003 | L. Ruchti et al. |
| 2003/0086073 A1 | 5/2003 | Braig et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0122647 A1 | 7/2003 | Ou |

(56)         References Cited

U.S. PATENT DOCUMENTS

| | | |
|---|---|---|
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0148024 A1 | 8/2003 | Kodas et al. |
| 2003/0163097 A1 | 8/2003 | Fleury et al. |
| 2003/0170436 A1 | 9/2003 | Sumi et al. |
| 2003/0175806 A1 | 9/2003 | Rule et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman et al. |
| 2003/0221621 A1 | 12/2003 | Pokharna et al. |
| 2004/0001027 A1 | 1/2004 | Killen et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064088 A1 | 4/2004 | Gorman et al. |
| 2004/0064259 A1 | 4/2004 | Haaland et al. |
| 2004/0068224 A1 | 4/2004 | Couvillon et al. |
| 2004/0069004 A1 | 4/2004 | Gist et al. |
| 2004/0069044 A1 | 4/2004 | Lavi et al. |
| 2004/0087904 A1 | 5/2004 | Langley et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0134609 A1 | 6/2005 | Yu |
| 2005/0137573 A1 | 6/2005 | Mclaughlin |
| 2005/0171503 A1 | 8/2005 | Van et al. |
| 2005/0182306 A1 | 8/2005 | Sloan |
| 2005/0182366 A1 | 8/2005 | Vogt et al. |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dianni et al. |
| 2005/0261660 A1 | 11/2005 | Choi |
| 2005/0262451 A1 | 11/2005 | Remignanti et al. |
| 2005/0272640 A1 | 12/2005 | Doyle et al. |
| 2005/0277912 A1 | 12/2005 | John |
| 2006/0009727 A1 | 1/2006 | O'Mahony et al. |
| 2006/0041229 A1 | 2/2006 | Garibotto et al. |
| 2006/0064053 A1 | 3/2006 | Bollish et al. |
| 2006/0079765 A1 | 4/2006 | Neer et al. |
| 2006/0079809 A1 | 4/2006 | Goldberger et al. |
| 2006/0086994 A1 | 4/2006 | Mefers et al. |
| 2006/0100494 A1 | 5/2006 | Kroll |
| 2006/0134323 A1 | 6/2006 | O'Brien |
| 2006/0134491 A1 | 6/2006 | Hilchenko et al. |
| 2006/0167350 A1 | 7/2006 | Monfre et al. |
| 2006/0173406 A1 | 8/2006 | Hayes et al. |
| 2006/0178633 A1 | 8/2006 | Garibotto et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0100635 A1 | 5/2007 | Mahajan et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0166453 A1 | 7/2007 | Van et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0259768 A1 | 11/2007 | Kear et al. |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0033320 A1 | 2/2008 | Racchini et al. |
| 2008/0051738 A1 | 2/2008 | Griffin |
| 2008/0051764 A1 | 2/2008 | Dent et al. |
| 2008/0058625 A1 | 3/2008 | Mcgarraugh et al. |
| 2008/0065050 A1 | 3/2008 | Sparks et al. |
| 2008/0071157 A1 | 3/2008 | Mcgarraugh et al. |
| 2008/0071158 A1 | 3/2008 | Mcgarraugh et al. |
| 2008/0078400 A1 | 4/2008 | Martens et al. |
| 2008/0097289 A1 | 4/2008 | Steil et al. |
| 2008/0114304 A1 | 5/2008 | Nalesso et al. |
| 2008/0132880 A1 | 6/2008 | Buchman |
| 2008/0160492 A1 | 7/2008 | Campbell et al. |
| 2008/0161664 A1 | 7/2008 | Mastrototaro et al. |
| 2008/0172026 A1 | 7/2008 | Blomquist |
| 2008/0172028 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0212966 A1 | 8/2009 | Panduro |

(56) References Cited

U.S. PATENT DOCUMENTS

| | | |
|---|---|---|
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2009/0326472 A1 | 12/2009 | Carter et al. |
| 2010/0017141 A1 | 1/2010 | Campbell et al. |
| 2010/0036326 A1 | 2/2010 | Matusch |
| 2010/0057042 A1 | 3/2010 | Hayter |
| 2010/0064243 A1 | 3/2010 | Buck et al. |
| 2010/0077198 A1 | 3/2010 | Buck et al. |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0145272 A1 | 6/2010 | Cefai et al. |
| 2010/0152658 A1 | 6/2010 | Hanson et al. |
| 2010/0174228 A1 | 7/2010 | Buckingham et al. |
| 2010/0185183 A1 | 7/2010 | Alme et al. |
| 2010/0211003 A1 | 8/2010 | Sundar et al. |
| 2010/0228110 A1 | 9/2010 | Tsoukalis |
| 2010/0241066 A1 | 9/2010 | Hansen et al. |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0009813 A1* | 1/2011 | Rankers ............ A61B 5/15087 604/66 |
| 2011/0021584 A1 | 1/2011 | Berggren et al. |
| 2011/0028817 A1 | 2/2011 | Jin et al. |
| 2011/0049394 A1 | 3/2011 | De Rochemont |
| 2011/0054390 A1 | 3/2011 | Searle et al. |
| 2011/0054399 A1 | 3/2011 | Chong et al. |
| 2011/0065224 A1 | 3/2011 | Bollman et al. |
| 2011/0071765 A1 | 3/2011 | Yodfat et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0124521 A1 | 5/2012 | Guo |
| 2012/0136336 A1 | 5/2012 | Mastrototaro et al. |
| 2012/0150446 A1 | 6/2012 | Chang et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0250449 A1 | 10/2012 | Nakano |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian et al. |
| 2013/0172695 A1 | 7/2013 | Nielsen et al. |
| 2013/0172710 A1 | 7/2013 | Mears et al. |
| 2013/0178791 A1 | 7/2013 | Javitt |
| 2013/0231642 A1 | 9/2013 | Doyle et al. |
| 2013/0245545 A1 | 9/2013 | Arnold et al. |
| 2013/0253472 A1 | 9/2013 | Cabiri |
| 2013/0261406 A1 | 10/2013 | Rebec et al. |
| 2013/0296792 A1 | 11/2013 | Cabiri |
| 2013/0296823 A1 | 11/2013 | Melker et al. |
| 2013/0298080 A1 | 11/2013 | Griffin et al. |
| 2013/0317753 A1 | 11/2013 | Kamen et al. |
| 2013/0332874 A1 | 12/2013 | Rosinko et al. |
| 2013/0338576 A1 | 12/2013 | O'Connor et al. |
| 2013/0346858 A1 | 12/2013 | Neyrinck |
| 2014/0005633 A1 | 1/2014 | Finan |
| 2014/0018730 A1 | 1/2014 | Stephan |
| 2014/0032549 A1 | 1/2014 | Mcdaniel et al. |
| 2014/0066859 A1 | 3/2014 | Ogawa et al. |
| 2014/0066886 A1 | 3/2014 | Roy et al. |
| 2014/0074033 A1 | 3/2014 | Sonderegger et al. |
| 2014/0088428 A1 | 3/2014 | Yang et al. |
| 2014/0108046 A1 | 4/2014 | Echeverria et al. |
| 2014/0121635 A1 | 5/2014 | Hayter |
| 2014/0127048 A1 | 5/2014 | Diianni et al. |
| 2014/0128839 A1 | 5/2014 | Diianni et al. |
| 2014/0129951 A1 | 5/2014 | Amin et al. |
| 2014/0135880 A1 | 5/2014 | Baumgartner et al. |
| 2014/0142508 A1 | 5/2014 | Diianni et al. |
| 2014/0146202 A1 | 5/2014 | Boss et al. |
| 2014/0171901 A1 | 6/2014 | Langsdorf et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birtwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0025503 A1 | 1/2015 | Searle et al. |
| 2015/0041498 A1 | 2/2015 | Kakiuchi et al. |
| 2015/0120317 A1 | 4/2015 | Mayou et al. |
| 2015/0134265 A1 | 5/2015 | Kohlbrecher et al. |
| 2015/0134353 A1 | 5/2015 | Ferrell et al. |
| 2015/0165119 A1 | 6/2015 | Palerm et al. |
| 2015/0173674 A1 | 6/2015 | Hayes et al. |
| 2015/0193585 A1 | 7/2015 | Sunna |
| 2015/0202386 A1 | 7/2015 | Brady et al. |
| 2015/0205509 A1 | 7/2015 | Scriven et al. |
| 2015/0205511 A1 | 7/2015 | Mnna et al. |
| 2015/0207626 A1* | 7/2015 | Neftel ................... G16H 40/67 713/168 |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0301691 A1 | 10/2015 | Qin |
| 2015/0306314 A1 | 10/2015 | Doyle et al. |
| 2015/0331995 A1 | 11/2015 | Zhao et al. |
| 2015/0351671 A1 | 12/2015 | Vanslyke et al. |
| 2015/0351672 A1 | 12/2015 | Vanslyke et al. |
| 2015/0356250 A1 | 12/2015 | Polimeni |
| 2015/0366945 A1 | 12/2015 | Greene |
| 2016/0015891 A1 | 1/2016 | Papiorek |
| 2016/0019352 A1 | 1/2016 | Cohen et al. |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0220181 A1 | 8/2016 | Rigoard et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0259889 A1 | 9/2016 | Murtha et al. |
| 2016/0287512 A1 | 10/2016 | Cooper et al. |
| 2016/0302054 A1 | 10/2016 | Kimura et al. |

(56) References Cited

U.S. PATENT DOCUMENTS

| | | |
|---|---|---|
| 2016/0331310 A1 | 11/2016 | Kovatchev |
| 2016/0354543 A1 | 12/2016 | Cinar et al. |
| 2017/0007882 A1 | 1/2017 | Werner |
| 2017/0021096 A1 | 1/2017 | Cole et al. |
| 2017/0049386 A1 | 2/2017 | Abraham et al. |
| 2017/0131887 A1 | 5/2017 | Kim et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0188943 A1 | 7/2017 | Braig et al. |
| 2017/0189625 A1 | 7/2017 | Cirillo et al. |
| 2017/0216524 A1 | 8/2017 | Haider et al. |
| 2017/0220751 A1* | 8/2017 | Davis ............... A61M 5/14244 |
| 2017/0239415 A1 | 8/2017 | Hwang et al. |
| 2017/0258987 A1 | 9/2017 | Caspers |
| 2017/0281877 A1 | 10/2017 | Marlin et al. |
| 2017/0286614 A1* | 10/2017 | Morris ................... A61B 5/742 |
| 2017/0296746 A1 | 10/2017 | Chen et al. |
| 2017/0311903 A1 | 11/2017 | Davis et al. |
| 2017/0332952 A1 | 11/2017 | Desborough et al. |
| 2017/0347971 A1 | 12/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrsio |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0307515 A1 | 10/2018 | Meller et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0095052 A1 | 3/2019 | De et al. |
| 2019/0132801 A1 | 5/2019 | Kamath et al. |
| 2019/0184091 A1 | 6/2019 | Sjolund et al. |
| 2019/0240403 A1 | 8/2019 | Palerm et al. |
| 2019/0290844 A1 | 9/2019 | Monirabbasi et al. |
| 2019/0321545 A1 | 10/2019 | Saint |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2019/0374714 A1 | 12/2019 | Rioux et al. |
| 2020/0001006 A1 | 1/2020 | Pizzochero et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0113515 A1 | 4/2020 | O'Connor et al. |
| 2020/0175208 A1* | 6/2020 | Yu ........................ G06F 21/6218 |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |
| 2022/0105270 A1 | 4/2022 | Doyle et al. |

FOREIGN PATENT DOCUMENTS

| | | | |
|---|---|---|---|
| CA | 1040271 | A | 10/1978 |
| CA | 3026851 | A1 | 2/2020 |
| CN | 1297140 | A | 5/2001 |
| CN | 101208699 | A | 6/2008 |
| DE | 4200595 | A1 | 7/1993 |
| DE | 19756872 | A1 | 7/1999 |
| EP | 0026056 | A1 | 4/1981 |
| EP | 0341049 | A2 | 11/1989 |
| EP | 0496305 | A2 | 7/1992 |
| EP | 0549341 | A1 | 6/1993 |
| EP | 0867196 | A2 | 9/1998 |
| EP | 0939451 | A1 | 9/1999 |
| EP | 1376759 | A2 | 1/2004 |
| EP | 1177802 | B1 | 9/2004 |
| EP | 1491144 | A1 | 12/2004 |
| EP | 1571582 | A2 | 9/2005 |
| EP | 0801578 | B1 | 7/2006 |
| EP | 2139382 | A1 | 1/2010 |
| EP | 2397181 | A1 | 12/2011 |
| EP | 2468338 | A1 | 6/2012 |
| EP | 2666520 | A1 | 11/2013 |
| EP | 2695573 | A2 | 2/2014 |
| EP | 2703024 | A1 | 3/2014 |
| EP | 2830499 | A1 | 2/2015 |
| EP | 2897071 | A1 | 7/2015 |
| EP | 2943149 | A1 | 11/2015 |
| EP | 3177344 | A1 | 6/2017 |
| EP | 3193979 | A1 | 7/2017 |
| EP | 3314548 | A1 | 5/2018 |
| EP | 3607985 | A1 | 2/2020 |
| FR | 2096275 | A5 | 2/1972 |
| GB | 1125897 | A | 9/1968 |
| GB | 2443261 | A | 4/2008 |
| JP | 51-125993 | A | 11/1976 |
| JP | 02-131777 | A | 5/1990 |
| JP | 2004-283378 | A | 10/2004 |
| JP | 2005-326943 | A | 11/2005 |
| JP | 2007-525276 | A | 9/2007 |
| JP | 2008-513142 | A | 5/2008 |
| JP | 2012-527981 | A | 11/2012 |
| JP | 2017-516548 | A | 6/2017 |
| JP | 2017-525451 | A | 9/2017 |
| JP | 2018-153569 | A | 10/2018 |
| JP | 2019-525276 | A | 9/2019 |
| TW | 200740148 | A | 10/2007 |
| TW | M452390 | U | 5/2013 |
| WO | 86/06796 | A1 | 11/1986 |
| WO | 98/00193 | A1 | 1/1998 |
| WO | 98/55073 | A1 | 12/1998 |
| WO | 99/10040 | A1 | 3/1999 |
| WO | 99/10049 | A1 | 3/1999 |
| WO | 99/56803 | A1 | 11/1999 |
| WO | 99/62576 | A1 | 12/1999 |
| WO | 00/30705 | A1 | 6/2000 |
| WO | 00/32258 | A1 | 6/2000 |
| WO | 00/48112 | A2 | 8/2000 |
| WO | 01/72354 | A2 | 10/2001 |
| WO | 01/78812 | A1 | 10/2001 |
| WO | 02/15954 | A1 | 2/2002 |
| WO | 02/26282 | A2 | 4/2002 |
| WO | 02/43866 | A2 | 6/2002 |
| WO | 02/76535 | A1 | 10/2002 |
| WO | 02/82990 | A1 | 10/2002 |
| WO | 03/16882 | A1 | 2/2003 |
| WO | 03/39362 | A1 | 5/2003 |
| WO | 03/45233 | A1 | 6/2003 |
| WO | 03/97133 | A1 | 11/2003 |
| WO | 2004/043250 | A1 | 5/2004 |
| WO | 2004/092715 | A1 | 10/2004 |
| WO | 2005/051170 | A2 | 6/2005 |
| WO | 2005/082436 | A1 | 9/2005 |
| WO | 2005/110601 | A1 | 11/2005 |
| WO | 2005/113036 | A1 | 12/2005 |
| WO | 2006/053007 | A2 | 5/2006 |
| WO | 2007/064835 | A2 | 6/2007 |
| WO | 2007/066152 | A2 | 6/2007 |
| WO | 2007/078937 | A2 | 7/2007 |
| WO | 2008/024810 | A2 | 2/2008 |
| WO | 2008/029403 | A | 3/2008 |
| WO | 2008/133702 | A1 | 11/2008 |
| WO | 2009/039203 | A2 | 3/2009 |
| WO | 2009/045462 | A1 | 4/2009 |
| WO | 2009/049252 | A1 | 4/2009 |
| WO | 2009/066287 | A2 | 5/2009 |
| WO | 2009/066288 | A1 | 5/2009 |
| WO | 2009/098648 | A2 | 8/2009 |

(56) References Cited

FOREIGN PATENT DOCUMENTS

| WO | 2009/134380 A2 | 11/2009 |
| WO | 2010/022069 A2 | 2/2010 |
| WO | 2010/053702 A1 | 5/2010 |
| WO | 2010/077279 A1 | 7/2010 |
| WO | 2010/132077 A1 | 11/2010 |
| WO | 2010/138848 A1 | 12/2010 |
| WO | 2010/139793 A1 | 12/2010 |
| WO | 2010/147659 A2 | 12/2010 |
| WO | 2011/031458 A1 | 3/2011 |
| WO | 2011/075042 A1 | 6/2011 |
| WO | 2011/095483 A1 | 8/2011 |
| WO | 2011/133823 A1 | 10/2011 |
| WO | 2012/045667 A2 | 4/2012 |
| WO | 2012/073032 A1 | 6/2012 |
| WO | 2012/108959 A1 | 8/2012 |
| WO | 2012/134588 A1 | 10/2012 |
| WO | 2012/177353 A1 | 12/2012 |
| WO | 2012/178134 A2 | 12/2012 |
| WO | 2013/050535 A2 | 4/2013 |
| WO | 2013/078200 A1 | 5/2013 |
| WO | 2013/134486 A2 | 9/2013 |
| WO | 2013/149186 A1 | 10/2013 |
| WO | 2013/177565 A1 | 11/2013 |
| WO | 2013/182321 A1 | 12/2013 |
| WO | 2014/029416 A1 | 2/2014 |
| WO | 2014/035672 A2 | 3/2014 |
| WO | 2014/109898 A1 | 7/2014 |
| WO | 2014/110538 A1 | 7/2014 |
| WO | 2014/149357 A1 | 9/2014 |
| WO | 2014/179774 A1 | 11/2014 |
| WO | 2014/194183 A2 | 12/2014 |
| WO | 2015/056259 A1 | 4/2015 |
| WO | 2015/061493 A1 | 4/2015 |
| WO | 2015/073211 A1 | 5/2015 |
| WO | 2015/081337 A2 | 6/2015 |
| WO | 2015/117082 A1 | 8/2015 |
| WO | 2015/117854 A1 | 8/2015 |
| WO | 2015/167201 A1 | 11/2015 |
| WO | 2015/177082 A1 | 11/2015 |
| WO | 2015/187366 A1 | 12/2015 |
| WO | 2016/004088 A1 | 1/2016 |
| WO | 2016/022650 A1 | 2/2016 |
| WO | 2016/041873 A1 | 3/2016 |
| WO | 2016/089702 A1 | 6/2016 |
| WO | 2016/141082 A1 | 9/2016 |
| WO | 2016/161254 A1 | 10/2016 |
| WO | 2017/004278 A1 | 1/2017 |
| WO | 2017/091624 A1 | 6/2017 |
| WO | 2017/105600 A1 | 6/2017 |
| WO | 2017/184988 A1 | 10/2017 |
| WO | 2017/187177 A1 | 11/2017 |
| WO | 2017/205816 A1 | 11/2017 |
| WO | 2018/009614 A1 | 1/2018 |
| WO | 2018/067748 A1 | 4/2018 |
| WO | 2018/120104 A1 | 7/2018 |
| WO | 2018/136799 A1 | 7/2018 |
| WO | 2018/204568 A1 | 11/2018 |
| WO | 2019/077482 A1 | 4/2019 |
| WO | 2019/094440 A1 | 5/2019 |
| WO | 2019/213493 A1 | 11/2019 |
| WO | 2019/246381 A1 | 12/2019 |
| WO | 2020/081393 A1 | 4/2020 |
| WO | 2021/011738 A1 | 1/2021 |

OTHER PUBLICATIONS

Levine et al. ("Companion Medical's Bluetooth-Enabled Insulin Pen and App Cleared by the FDA". https://diatribe.org/companion-medical-bluetooth-enabled-insulin-pen-app-cleared-fda, Aug. 30, 2016 (Year: 2016).*

Kwon et al. ("New Apps and Devices at DiabetesMine D-Data Exchange and Innovation Summit". https://diatribe.org/new-apps-and-devices-diabetesmine-d-data-exchange-and-innovation-summit, , Dec. 8, 2017) (Year: 2017).*

* cited by examiner

Therapy Management App sends the instruction with a signature

Therapy Management App sends the
instruction with a signature

300

Trusted Auth Service sends the signature

Trusted Auth Service sends the signature

**Delivery Device Requests the
Signature from Mobile Device**

Delivery Device Requests the
Signature from Mobile Device

600

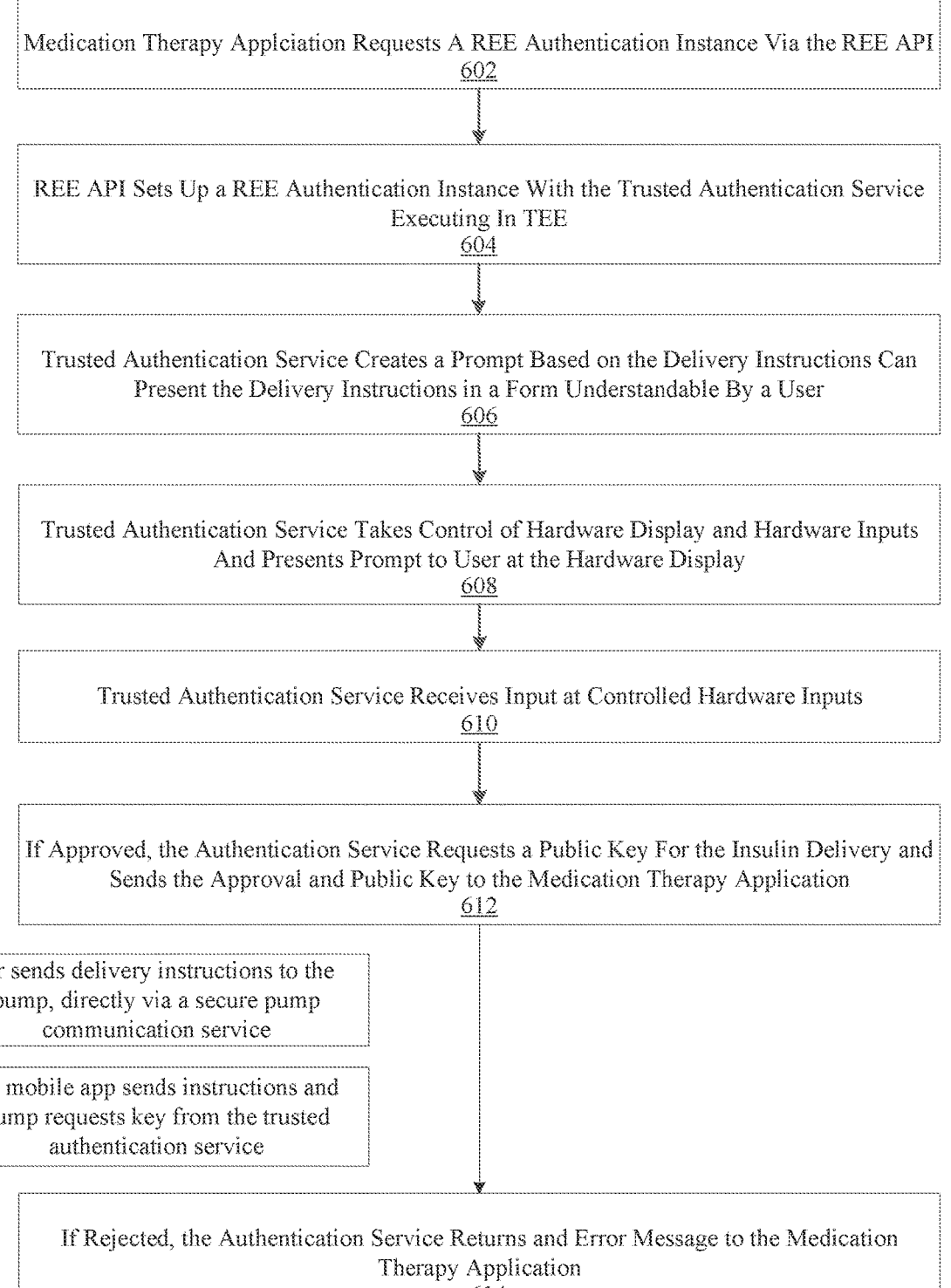

Medication Therapy Applciation Requests A REE Authentication Instance Via the REE API
602

REE API Sets Up a REE Authentication Instance With the Trusted Authentication Service
Executing In TEE
604

Trusted Authentication Service Creates a Prompt Based on the Delivery Instructions Can
Present the Delivery Instructions in a Form Understandable By a User
606

Trusted Authentication Service Takes Control of Hardware Display and Hardware Inputs
And Presents Prompt to User at the Hardware Display
608

Trusted Authentication Service Receives Input at Controlled Hardware Inputs
610

If Approved, the Authentication Service Requests a Public Key For the Insulin Delivery and
Sends the Approval and Public Key to the Medication Therapy Application
612

Or sends delivery instructions to the
pump, directly via a secure pump
communication service Or mobile app sends instructions and
pump requests key from the trusted
authentication service If Rejected, the Authentication Service Returns and Error Message to the Medication
Therapy Application
614

*FIGURE 6*

880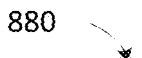
Press power button and release to confirm  >
Cancel  >
Android Protected Confirmation
Confirm bolus in the amount of 1.5 units.
This confirmation provides an extra layer of security for
the action you're about to take.
*FIGURE 8D*

950
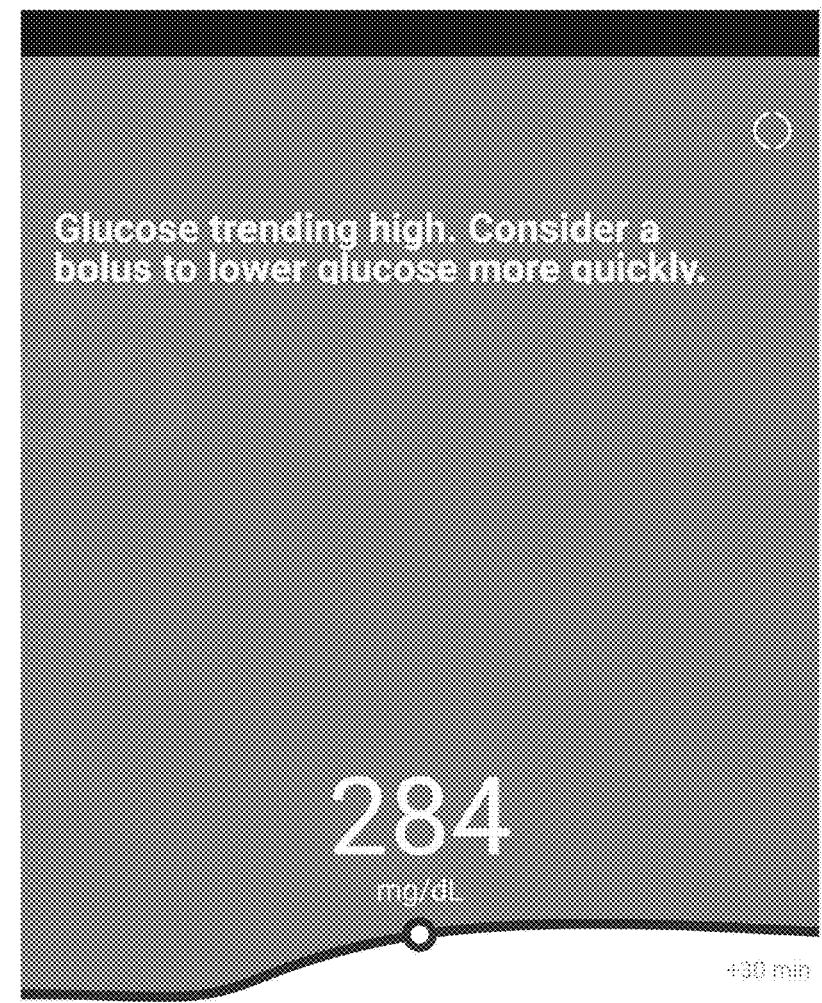
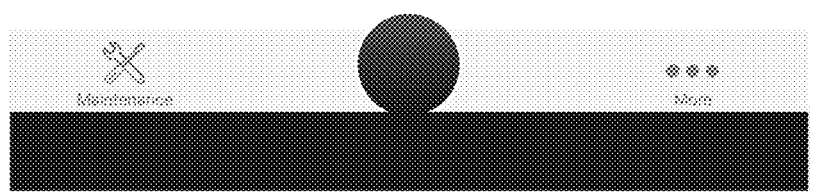
*FIGURE 9B*

1100

Select a Carb amount
Select one or tap and hold to adjust 20g     40g     60g

Correction or Insulin Only

*FIGURE 11*

Crypto-Key Storage
112

Authenticator 114

Delivery Controller
116

Request authentication of
change request 1222

Retrieve private key(s) 1224

Compare keys 1226

Send Result 1228

If instructions verified
then adjust set points 1230

If instructions not verified do
not adjust set points 1232

A

1200

COMPUTING ARCHITECTURE FOR ASSURING THE PROVENANCE OF MEDICATION THERAPY RELATED PARAMETERS, AND RELATED SYSTEMS, METHODS AND DEVICES

CROSS-REFERENCE TO RELATED APPLICATION

This application claims the benefit under 35 U.S.C. § 119 (e) of U.S. Provisional Patent Application Ser. No. 62/669, 250, filed May 9, 2018, the disclosure of which is hereby incorporated herein in its entirety by this reference.

TECHNICAL FIELD

This disclosure generally relates to medication delivery systems, and more specifically, some embodiments relate to a mobile computing device that may setup a secure, trusted, process for a user to confirm medication therapy parameters at the mobile computing device and certify that a medication therapy parameter was confirmed using such a process.

BACKGROUND

Infusion pumps can be used to deliver fluids, such as medications, into a patient's body in a controlled manner and/or upon demand. Infusion pumps can be implanted, transcutaneous, or external. Infusion pumps be programmed to provide a continuous or near continuous deliver of fluid and/or programmed to deliver the fluid according to a control algorithm. Infusion pumps can also be used by a user (e.g., patient, caregiver, or healthcare professional) to deliver boluses of medication upon demand.

There are many different types of infusion pumps, which are used for a variety of purposes and in a variety of environments. Infusion pumps may be capable of delivering fluids in large or small amounts, and may be used to deliver nutrients or medications-such as insulin or other hormones, antibiotics, chemotherapy drugs, and pain relievers. Infusion pumps may operate "open loop" (e.g., operation is at least partially at the discretion of a user), and "closed loop" (e.g., the measuring, adjustment of parameters, and insulin delivery occurs without user intervention, i.e., at the discretion of the control system). Infusion pumps typically have user interfaces right on the infusion pump or come with a specialized remote communication device specifically for that infusion pump, thus the act of programming the infusion pump or requesting a bolus of medication when in public can result in unwanted attention on the patient. Additionally, specialized devices can burden a patient by requiring that the patient carry around an extra device on top of the devices that the user already carries around anyways.

BRIEF DESCRIPTION OF THE DRAWINGS

The purpose and advantages of the various embodiments of the disclosure will be apparent to one of ordinary skill in the art from the detailed description in conjunction with the following appended figures:

FIG. 6 shows a flowchart of a confirmation process executed in the TEE, according to embodiments of the disclosure;

FIGS. 8A-8D show exemplary user interfaces for an insulin therapy application that may be used to calculate a bolus, according to embodiments of the disclosure;

FIG. 9B shows an example of a recommendation provided by the insulin delivery unit to the mobile computing device to bolus in response to a trend toward higher blood glucose levels that may trigger the confirmation process shown in FIG. 9A, according to an embodiment of the disclosure;

FIG. 11 shows an example of a user interface where the user, instead of entering the amount of carbs selects a meal or carbohydrate amount associated with a meal-type that the user entered, according to an embodiment of the disclosure.

DETAILED DESCRIPTION

Figure 1:
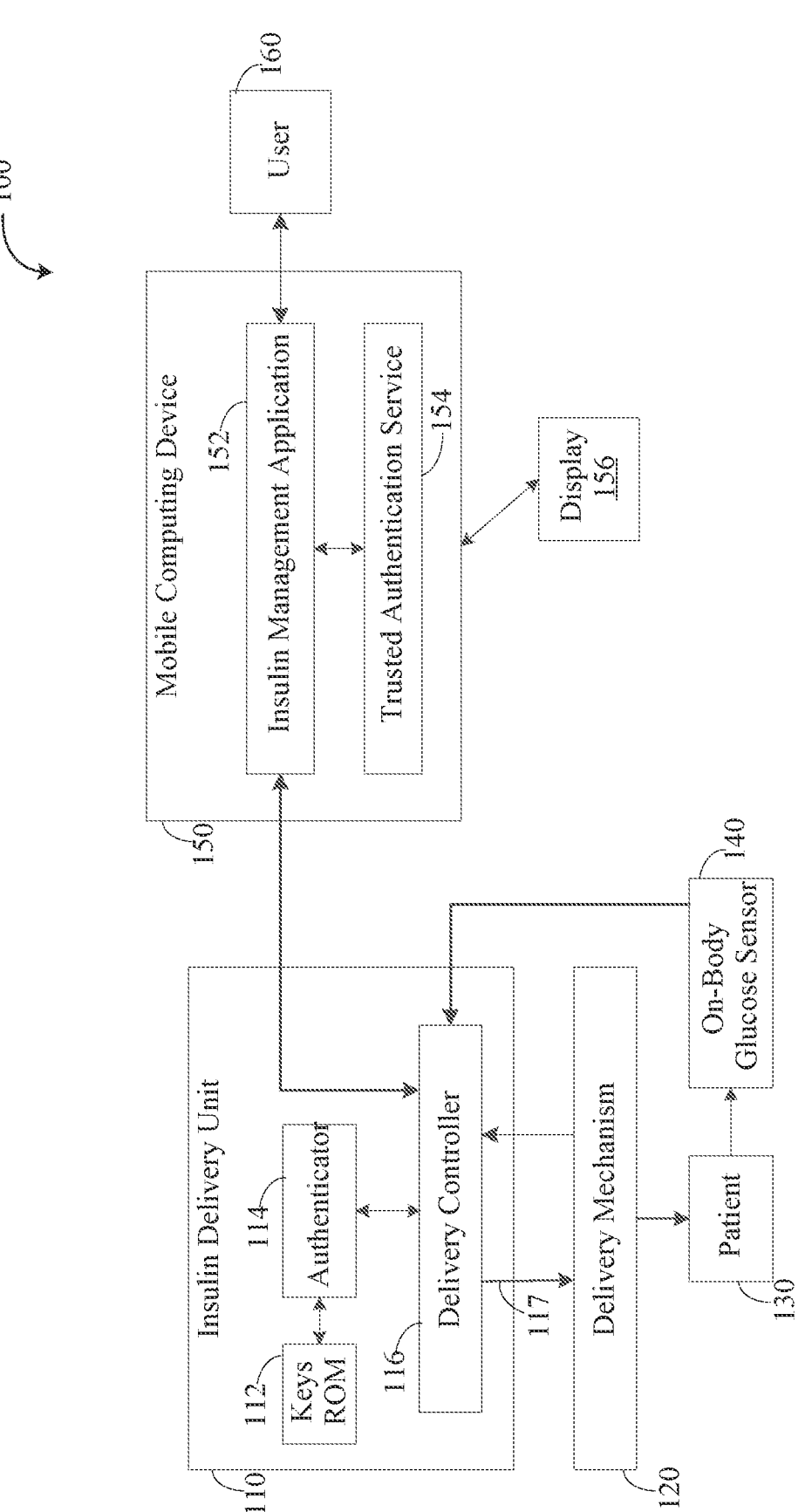
FIG. 1 shows an embodiment of an insulin therapy system configured to implement embodiments of the disclosure.

The following description provides specific details to provide a thorough description of various embodiments of the invention. However, one of ordinary skill in the art will understand that the disclosed embodiments may be practiced without using these specific details. Indeed, the disclosed embodiments may be practiced in conjunction with conventional systems and methods used in the industry. In addition, only those elements helpful to understand and enable one of ordinary skill in the art to practice the disclosed embodiments are described in detail. One of ordinary skill in the art will recognize that some elements not described herein but, using various conventional method components and acts, would be in accord with the embodiments of this disclosure.

The following description may include examples to help enable one of ordinary skill in the art to practice the disclosed embodiments. The use of the terms "exemplary," "by example," "for example," "e.g.," and "such as" means that the related description is explanatory and though the scope of the disclosure is intended to encompass the recited examples and their legal equivalents. The use of such terms is not intended to limit the scope of an embodiment or this disclosure to the specified components, steps, features, functions, arrangement of components, or the like. Moreover, the use of such terms does not indicate or imply that the related description comprises, or is, a preferred embodiment.

Any drawings accompanying this disclosure are for illustrative purposes only, and no scale is intended unless specifically indicated. Elements common among figures may retain the same numerical designation; however, the similarity in numbering does not mean that the structures or components are necessarily identical in size, composition, configuration, or any other property.

It will be readily understood that the components of the embodiments as generally described herein and illustrated in the drawing could be arranged and designed in a wide variety of different configurations. Thus, the following description of various embodiments is not intended to limit the scope of the present disclosure, but is merely representative of various embodiments. While the various aspects of the embodiments may be presented in drawings, the drawings are not necessarily drawn to scale unless specifically indicated.

As noted, above, specific implementations shown and described are only examples and should not be construed as the only way to implement the present disclosure unless specified otherwise herein. Elements, circuits, and functions may be shown in block diagram form in order not to obscure the present disclosure in unnecessary detail. Block definitions and partitioning of logic between various blocks is/are examples of a specific implementation. It will be readily apparent to one of ordinary skill in the art that the present disclosure may be practiced by numerous other partitioning solutions. For the most part, details concerning timing considerations and the like have been omitted where such details are not necessary to obtain a complete understanding of the present disclosure and are within the abilities of persons of ordinary skill in the relevant art.

Many of the functional units described in this specification may be illustrated, described or labeled as logic, modules, engines, threads, or other segregations of programming code, to more particularly emphasize their implementation independence in accomplishing the features, functions, tasks or steps that are generally described herein. The various illustrative logical blocks, modules, and circuits described in connection with the embodiments disclosed herein may be at least partially implemented or performed with a general purpose processor, a special purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein.

The functional units may be implemented using software or firmware, stored on a computer-readable storage medium, in system memory, or a combination thereof for execution by various types of processors. Some examples of languages that may be used to write the software include, but are not limited to, an extensible markup language, C, C++, JAVA, MATLAB, MINITAB, EXPRESS, DRAKON, DYNA, PYTHON, MOOSE, and RUBY. The software programs may be further translated into machine language or virtual machine instructions and stored in a program file in that form. The program file may then be stored on or in one or more of the articles of manufacture. Although enabling software might be "written on" a disc, "embodied in" an integrated circuit, "carried over" a communications circuit, "stored in" a memory chip, or "loaded in" a cache memory, it will be appreciated that, for the purposes of this application, the software is referred to simply as being "in" or "on" the computer readable medium. Thus, the terms "in" or "on" are intended to encompass the above mentioned and all equivalent and possible ways in which software can be associated with a computer readable medium.

In the case of a general-purpose computer, these logic and modules may be embodied in software classes and applications executed by processor cores, and while the modules are executing the general-purpose computer may be thought of as a special purpose computer or a specific purpose computer. The logic and modules may also relate to specific purpose hardware, including the firmware and machine code, controlling its operation. An identified module of executable code may, for instance, comprise one or more physical or logical blocks of computer instructions, which may, for instance, be organized as a thread, object, procedure, or function. Nevertheless, the executable code of an identified module need not be physically located together, but may comprise disparate instructions stored in different locations which, when joined logically together, comprise the module and achieve the stated purpose for the module.

A module of executable code may comprise a single instruction, or many instructions, and may even be distributed over several different code segments, among different programs, and across several storage or memory devices. Similarly, operational data may be identified and illustrated herein within modules, and may be embodied in any suitable form and organized within any suitable type of data structure. The operational data may be collected as a single data set or may be distributed over different locations including over different storage devices, and may exist, at least partially, merely as electronic signals on a system or network. Where a module or portions of a module are implemented in software, the software portions are stored on one or more physical devices, which are referred to herein as computer-readable media.

In some embodiments, the software portions are stored in a non-transitory state such that the software portions or representations thereof, persist in the same physical location for a period of time. Additionally, in some embodiments, the software portions are stored on one or more non-transitory storage mediums, which include hardware elements capable of storing non-transitory states and/or signals representative of the software portions, even though other portions of the non-transitory storage mediums may be capable of altering and/or transmitting the signals. Examples of non-transitory storage mediums are flash memory and certain types of random-access memory (RAM). Another example of a non-transitory storage medium includes a read-only memory (ROM) which can store signals and/or states representative of the software portions for a period of time. However, the ability to store the signals and/or states is not diminished by further functionality of transmitting signals that are the same as, or representative of, the stored signals and/or states. For example, a processor may access the ROM to obtain signals that are representative of the stored signals and/or states to execute the corresponding software instructions.

A general-purpose processor may be a microprocessor, but in the alternative, the processor may be any conventional processor, controller, microcontroller, or state machine. A processor may also be implemented as a combination of computing devices, such as a combination of a DSP and a microprocessor, a plurality of microprocessors, one or more microprocessors in conjunction with a DSP core, or any other such configuration. A general-purpose computer including a processor is considered a special-purpose computer when the general-purpose computer is configured to execute computing instructions (e.g., software code) related to embodiments of the present disclosure.

The embodiments disclosed herein may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be rearranged. A process may correspond to a method, a thread, a function, a procedure, a subroutine, a subprogram, etc. Furthermore, the methods disclosed herein may be implemented in hardware, software, or both. If implemented in software, the functions may be stored or transmitted as one or more instructions or code on computer-readable media. Computer-readable media includes both computer storage media and communication media including any medium that facilitates transfer of a computer program from one place to another.

Various embodiments described herein may be described as implemented in or by a "computer," "computing system," or a "computing platform," which are to be understood to include at least one non-transitory computer-readable medium and at least one processing unit. In general, the storage medium will store, at one time or another, at least portions of an executable program code, and a processor(s) will execute one or more of the instructions included in that executable program code.

It will be appreciated that the term "executable program code" and the term "software" mean substantially the same thing for the purposes of this description. It is not necessary to the practice of the various embodiments described herein that the storage medium and the processing unit be physically located in the same place. That is to say, it is foreseen that the processor and the memory might be distributed among physical pieces of equipment or even in geographically distinct locations. One of ordinary skill in the art will appreciate that "media," "medium," "storage medium," "computer-readable media," or "computer-readable medium" as used herein, may include a diskette, a magnetic tape, a digital tape, a compact disc, an integrated circuit, a ROM, a CD, DVD, Blu-Ray, a cartridge, flash memory, a PROM, a RAM, a memory stick or card, or any other non-destructive storage medium useable by computers, including those that are re-writable.

Although some insulin therapy systems have been designed and contemplated that use commercially available smartphones to send delivery instructions and other therapy parameters to insulin infusion pumps (referred to herein as simply an "insulin pump"), these smartphones may also be used to download third-party software of unknown provenance. The third-party software might be malware, render the smartphone susceptible to malware, or otherwise have security holes that renders the smartphone susceptible to cyber threats. Whether malware or buggy software, either might render a smartphone vulnerable to processes that cause it to send incorrect or unintended medication delivery instructions to the infusion pump controller, for example by interfering with calculations related to therapy management, making unauthorized changes to therapy parameters, hijacking the medication delivery instruction process, or causing a smartphone to send erroneous medication delivery instructions.

One way to compensate for the possibility of an erroneous delivery instruction is to have a user confirm a recommendation and delivery amount before it is sent. However, there is still the possibility that malicious software hijacked or interfered with the confirmation process.

Accordingly, there is a need for methods, systems, and devices that enable a mobile computing device that is otherwise able to download third-party software of unknown provenance to provide therapy related instructions (e.g., medication delivery instructions, user-specified therapy parameters, etc., and also referred to herein as "insulin therapy instructions") to a medication delivery device, where the medication device is assured the instructions were confirmed by a user. Further, in the case of a user confirmation, there is a need for methods, systems, and devices that provide additional confidence that a user, and not a malicious process, confirmed the therapy related instructions.

This disclosure describes, generally, systems and methods to provide a secure, trusted, user driven confirmation process at a mobile computing device for therapy related instructions, and provide assurances to a medication delivery device that receives the therapy related instructions that the instructions were confirmed by a user and, more specifically, were confirmed by user-action at the mobile computing device.

This disclosure also describes, generally, embodiments of computing architectures configured to implement the methods described, above. In some embodiments, computing architectures are configured to provide trusted medication therapy related instructions (e.g., medication delivery instructions, requests to change therapy parameters, etc.) from a mobile computing device (e.g., a smartphone, a tablet, etc.) to a medication delivery device (e.g., an insulin infusion pump). In particular, the computing architectures (and associated techniques, devices, hardware, and systems) enable a user to confirm the therapy related instructions (e.g., an instruction to deliver a bolus of insulin) using a user interface of a mobile computing device (or a wearable device connected to the mobile computing device), and certify (i.e., provide assurances) that a user confirmed a medication delivery instruction.

Some embodiments of computing architectures include a trusted execution environment (TEE) that enables a rich execution environment (REE) that makes available one or more trusted services to a therapy management application executing in an open (i.e., normal) execution environment within the computing architecture.

Using an example of medication delivery instructions determined at a therapy management application at the mobile computing device, a trusted authentication service may receive a request from a therapy management application related to, e.g., a medication delivery instruction intended for a medication delivery unit. In one embodiment, the message may include a text string that is in a format understandable to a user, for example, including a medication dose amount in units familiar to a user. In response to receiving the request, the TEE may take over a user interface and display and present a prompt to a user to confirm the medication delivery instructions. If the user confirms the medication delivery instruction, the trusted authentication service sends a confirmation message to the therapy management application together with a signature (e.g., a message hashed using a private key associated with the trusted service) that certifies the process by which the user confirmed the delivery instruction at the mobile computing device, and, more generally, provides assurances to the medication delivery device that the insulin delivery instruction was confirmed by user action.

The mobile device may send the medication delivery instructions to a medication delivery device (e.g., insulin pump) and a medication delivery controller verifies the signature. In one embodiment, the delivery controller verifies the signature using a previously provisioned public key associated with the TEE at the mobile computing device. Upon verification of the signature, the insulin pump controller executes the medication delivery instruction.

While some therapy related instructions are described herein in terms of a human understandable format (e.g., a dose amount), the delivery instructions that are executed by a control system may be provided such human understandable format (which the control system translates), in the form of a process variable or set-points, a range for a process variable, control actions, or the like. A control system may be configured to adjust its control actions responsive to the process variable or set-points.

While some embodiments and examples described in this disclosure relate to insulin therapies and insulin delivery, one of ordinary skill in the art would appreciate that the principles of the present disclosure are not limited to any specific type of insulin (e.g., rapid acting, long acting, or a mixture of the two), nor limited to insulin delivery or insulin therapy, more generally. One of ordinary skill in the art would also appreciate that the principles of the present disclosure are applicable to medication delivery and medication therapies, more generally.

Further, the embodiments of the disclosure are not limited to a specific type of medication delivery assembly or technique, and medication delivery includes injection type delivery, aerosolized delivery (e.g., inhaled), and intravenous delivery, and includes autonomous (e.g., an infusion-pump based closed-sloop delivery system), semi-autonomous (e.g., an infusion-pump open-loop based delivery system), and fully open loop systems (e.g., insulin pens, insulin inhalers).

FIG. 1 shows an embodiment of an insulin therapy system 100 configured to implement embodiments of the disclosure. An insulin delivery unit 110 is configured to control the automated delivery of insulin by delivery mechanism 120 to a patient 130. The patient 130 may have an optional on-body glucose sensor 140 (such as a continuous glucose monitor or a blood glucose monitor) that periodically provides blood glucose levels of the patient 130 to a delivery controller 116 of the insulin delivery unit 110. The delivery controller 116 may be configured to use the blood glucose levels as well as other environmental information (e.g., pump status, physiological disturbance information, etc.) to continuously make retrospective-based, risk-based, and/or fault-based adjustments for the dosing of insulin at the patient 130 and send control commands 117 to the delivery mechanism based on such adjustments. The insulin delivery unit 110 may be configured for closed-loop autonomous insulin delivery or open-loop semi-autonomous insulin delivery.

In one embodiment, the delivery mechanism 120 may be an infusion pump, and in one embodiment may include an infusion catheter adapted to subcutaneously deliver insulin under the skin of a patent 130 using an infusion set at an infusion site. In other embodiments, an insulin delivery unit can be or also include insulin pens, insulin syringes, and insulin inhalers.

In some embodiments, the blood glucose data based on measurements by the glucose sensor 140 may be provided to an insulin management application 152 executing on a mobile computing device 150 by the insulin delivery unit 110 or directly by the glucose sensor 140. The mobile computing device may be a smartphone or tablet and may be configured for wireless or wired communication with one or more of the insulin delivery unit 110 and glucose sensor 140, for example, by way of a protocol defined according to Wi-Fi, Bluetooth, Bluetooth Low Energy, and Near Field Communication. The insulin management application 152 may be configured to perform bullous determinations based on the received blood glucose data.

The mobile computing device 150 may also include one or more trusted authentication service 154 that, as described below, are configured to provide services to the insulin management application 152.

Calculations and adjustments for automated insulin delivery are described, generally, in U.S. Patent Publication No. 2017/0332952, published Nov. 23, 2017, and entitled "INSULIN DELIVERY SYSTEM AND METHODS WITH RISK BASED SET POINTS," the entire contents and disclosure of which are hereby incorporated herein by this reference.

In various embodiments, the user 160 and patient 130 may be the same person. However, the disclosure and embodiments described herein are not so limited. The user 160 may be a patient, a care giver, a patent, a clinician, or another medical service provider. The user 160 may also be a software application executing on a computing device or the cloud, which provides a therapy monitoring service.

Figure 2:
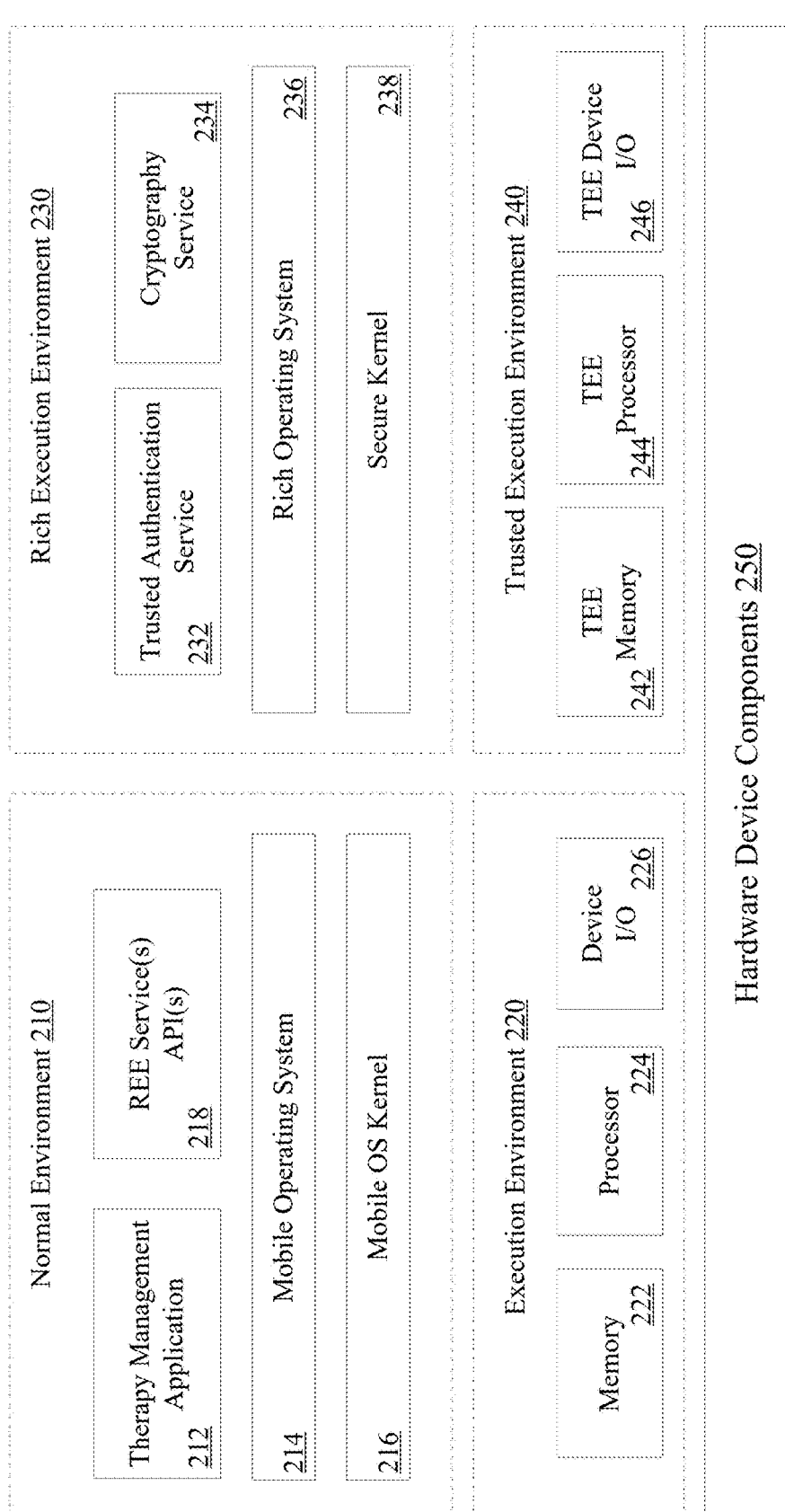
FIG. 2 shows an embodiment of a system architecture configured to implement the trusted authentication services FIG. 1.

FIG. 2 shows an embodiment of a system architecture 200 configured to implement the embodiments of trusted authentication services described herein, including the trusted authentication service 154 executing at the mobile computing device 150 of FIG. 1. The system architecture 200 includes a normal execution environment 210 and a rich execution environment (REE) 230. The normal execution environment 210 provides an environment for the therapy management application 212 (e.g., insulin management application 152) and applications of unknown provenance to execute. The mobile operating system 214 also executes within the normal execution environment 210, and the mobile OS kernel 216 provides the therapy management application 212 access to the resources of the execution environment 220, namely, the memory 222, processor 224, and device I/O 225. The device I/O 225 may be coupled to various hardware device components 250, for example, a display, speakers, wireless communication equipment, storage, etc.

The trusted execution environment (TEE) 240 includes a TEE processor 244, TEE memory 242, and TEE device I/O 246 that are isolated from the components of the normal execution environment 220. The TEE processor 244 may be secure cores of a main processor that includes processor 224, a separate microprocessor, or a virtualized instance of a main processor. In various embodiments, the TEE processor 244, TEE memory 242, and TEE device I/O 246 may be isolated from the rest of the system architecture 200, for example, using memory and I/O protection mechanisms supported by hardware.

A secure kernel 238 may be configured to access the TEE 240, and a rich operating system 236 may be configured to make system calls to the secure kernel 238, for example, using an application programming interface of the secure kernel 238. The rich operating system 236 enables further isolation of the TEE 240 and its hardware and software security resources from the mobile operating system 214 and applications executing in the normal execution environment 210. The rich operating system 236 may be part of a rich execution environment 230 that runs on top of the TEE 240, and may include trusted authentication service 232, cryptography service 234, and the secure kernel 238, mentioned above. Various trusted applications may execute in the REE 230, including applications that provide the trusted authentication service 232 and cryptography service 234, as well as other services not shown.

The therapy management applications 212 may access services provided within the REE 230 by way of the REE service(s) API(s) 218. These API's provide a limited interface for the therapy management application 212 to pass messages to, and receive messages from, services executing at the REE 230. The limited interface may be limited in terms of software, and also limited in terms of hardware isolation.

During the assembly of the insulin pump, in a controlled manufacturing environment, a number of cryptographic keys (e.g., private/public key pairs associated with the insulin delivery unit) may be loaded onto the insulin delivery unit 110 that allow the insulin delivery unit 110 to both verify authenticity of messages that it sends/receives and encrypt/decrypt messages that it sends/receives. In one embodiment, cryptographic keys are stored in ROM 112 (e.g., key ROM 112). These keys may be provided to the mobile computing device 150, an insulin management application 152 and/or one or more of the trusted authentication service 232. Further, during a provisioning process, the insulin delivery unit 110 may receive public keys from the mobile computing device and the TEE operating at the mobile computing device 150. In some cases, public/private key pairs may be associated with specific applications, for example, a therapy management application or a trusted authentication service.

Various examples of insulin therapies that incorporate a user confirmation according to a secure confirmation process established by the trusted authentication service implemented by insulin therapy system 100 and system architecture 200 are shown in FIGS. 3A, 3B, 4A, 4B, 5A, 5B, 12A and 12B. The processes may be initiated, for example, after a user indicates a meal, exercise, or another event that might affect a patient's blood glucose levels. By way of a user interface, the user may enter, for example, the number of grams of carbohydrates that the patient intends to eat and estimates about the patient's physiology. In one embodiment, the system may receive an indication that a user requested that the system provide a recommended bolus of insulin to account for the meal (i.e., changes in blood glucose due to the carbohydrate intake), in another embodiment, the system may calculate the recommendation without a user request (e.g., automatically responsive to therapy data received from the insulin delivery unit). The insulin management application 152 calculates insulin delivery instructions, and creates a recommendation(s) based on the instructions. In some embodiments the insulin management application 152 presents the recommendation(s) to the user 160 at a user interface and the user may confirm the recommendation or, if there are options, select an option, at the user interface.

Responsive to the input received at the user interface, the insulin management application 152 sends a request for a trusted user confirmation to the trusted authentication service 154. In one embodiment, the insulin management application 152 requests trusted user confirmation automatically. In another embodiment, the insulin management application 152 requests trusted user confirmation if the user confirmation includes a change to a recommended insulin delivery instructions (e.g., the user provides a different dose amount). The request may include a text string with a dose amount or some other format understandable to a user.

Responsive to the request, the trusted authentication service 154 establishes a secure user interaction process at the mobile computing device 150. In one embodiment, the trusted authentication service 154 exerts control over the display 156 and one or more hardware inputs of the mobile computing device 150, and presents the text string at the display along with instructions for a user action to confirm the instruction that includes manipulating the controlled hardware inputs. In one embodiment, the user may push a hardware button, such as the power button, that is monitored by the trusted authentication service 154 to provide the requested user action. In one embodiment, the confirmation instructions may include a user action conditions. For example, a user action condition may be a timing requirement for the user to manipulate the hardware buttons, such as asserting the power button hardware input for 2 seconds, 5 seconds, 10 seconds. Another user condition may be to assert the power button hardware input using a pattern or code such as long, short, short, long. Another user condition may be to assert the power button hardware input before a timer expires. One of ordinary skill in the art would understand that other hardware inputs may be used in addition to, or as an alternative to, the power button, for example, the volume button or a biometric sensor such as fingerprint sensors that are built into mobile devices and are configured to provide information about biometrics in the form of biometric data.

In one embodiment, the trusted authentication service 154 sends one of a success, time out, or failure message to the therapy management application. If the expected user action is received then the trusted authentication service 154 may generate a signature and return the signature with the success message. In one embodiment, the trusted authentication service 154 may generate the signature by hashing a message, including some or all of the success message, using its private key and/or the public key of the insulin delivery unit 110.

In one embodiment, the trusted authentication service 154 may be configured to provide one or more therapy specific services to the insulin management application 152. For example, in one embodiment, the trusted authentication service 154 may be configured to (or may be configured to call a trusted insulin therapy specific application that is configured to) check that the dose amount in a text string matches a delivery instruction calculated by the insulin management application 152. If the dose amount does not match the delivery instruction, it may be corrected or it may generate a request that the insulin management application 152 resubmit its authentication request.

Upon receiving the success message and signature, the insulin management application 152 provides the delivery instructions and signature to the insulin delivery unit 110. In one embodiment, the insulin management application 152 may communicate the delivery instruction and signature to the insulin delivery unit 110 using a secure communication protocol, and the mobile computing device 150 and insulin delivery unit 110 may include a communication architecture to implement the protocol, such as is described in U.S. patent application Ser. No. 15/431,452, filed Feb. 13, 2017, entitled SECURE COMMUNICATION ARCHITECTURE FOR MEDICAL DEVICES, the entire contents and disclosure of which are hereby incorporated herein by this reference.

If the signature is verified then that confirms to the insulin delivery unit 110 that the delivery instructions received with the signature were confirmed by user action.

11

Figure 3A:
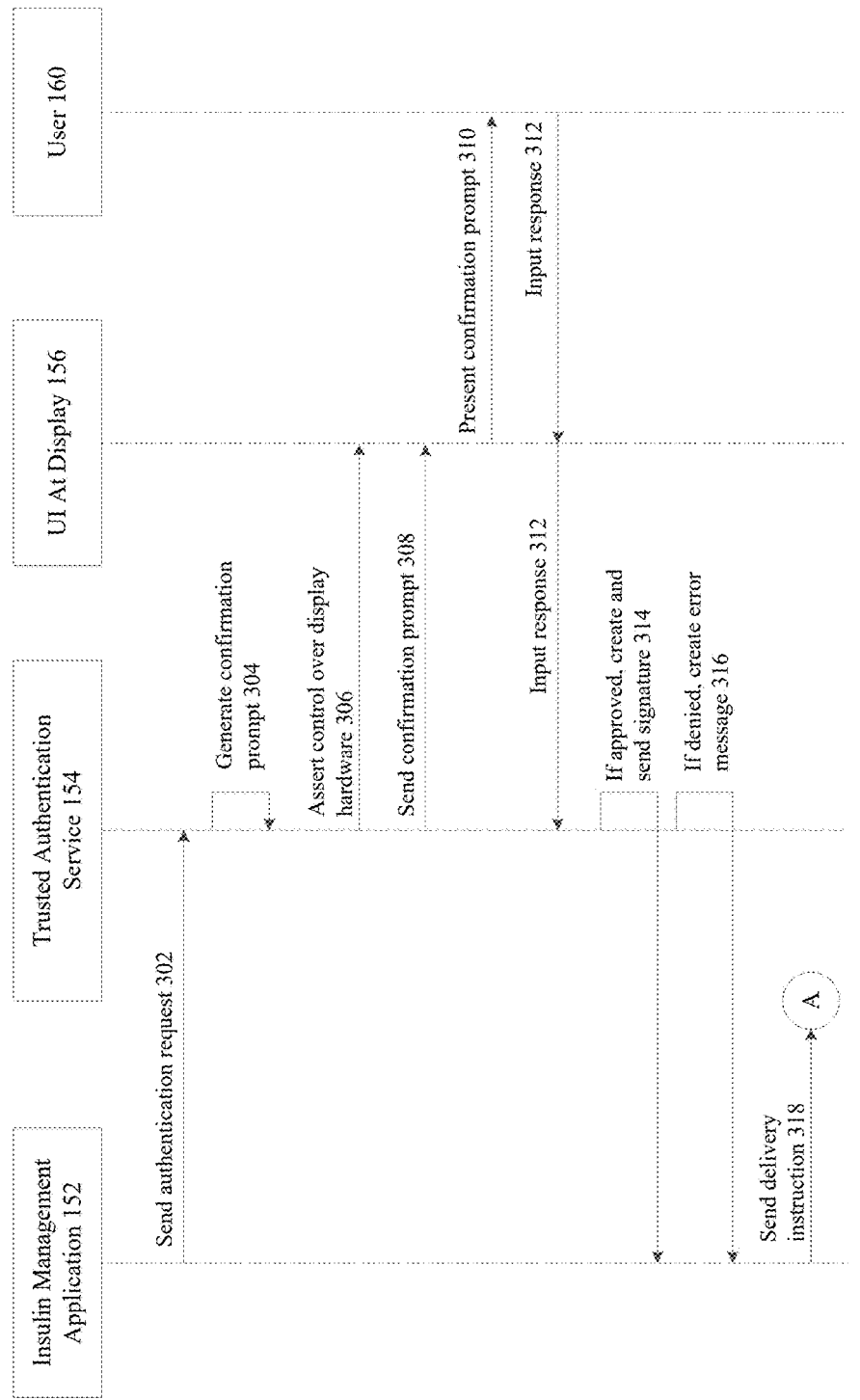
FIGS. 3A and 3B show an embodiment where the insulin management application sends an insulin delivery instruction and a signature to the insulin delivery unit.
Figure 3B:
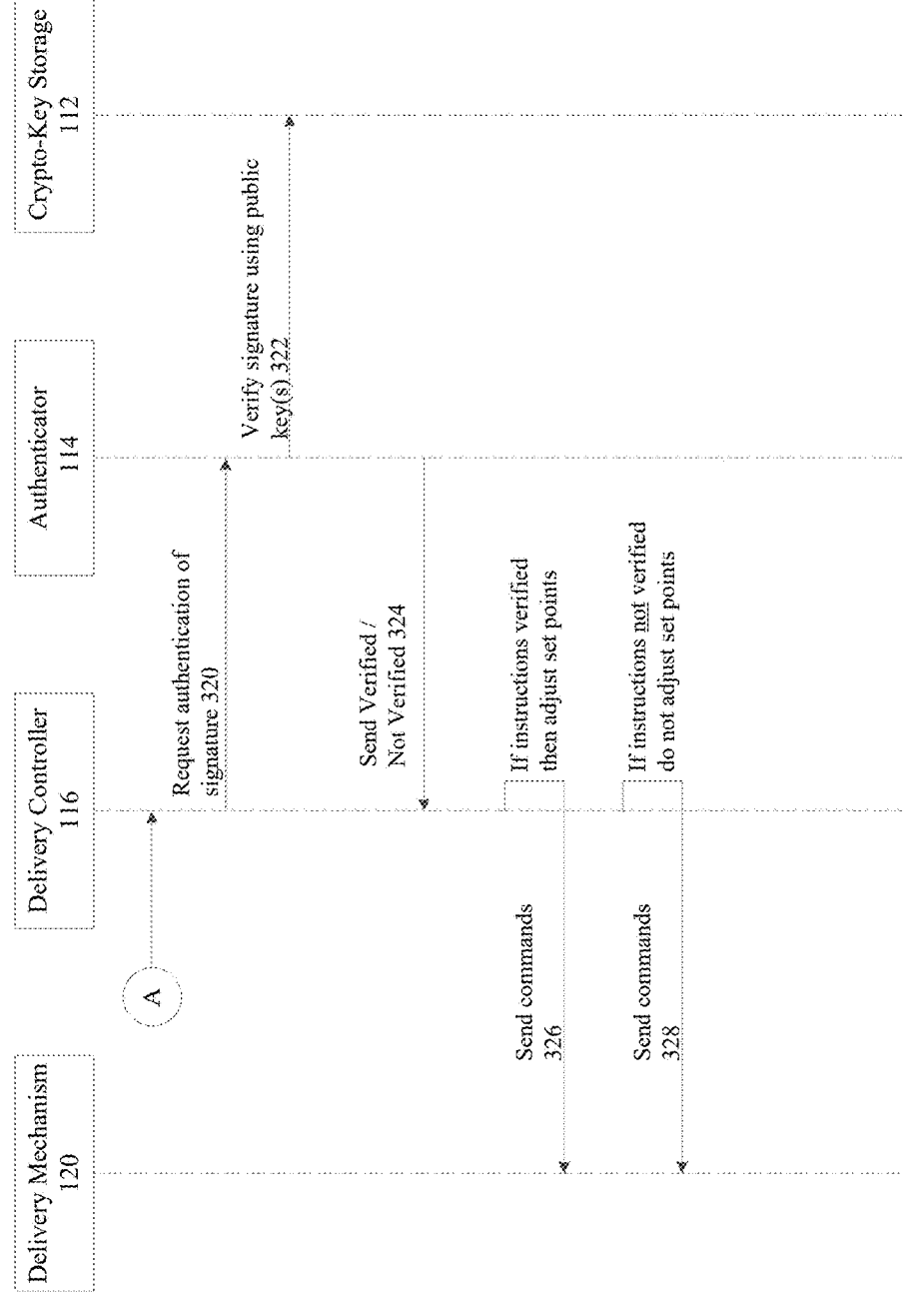

FIGS. 3A and 3B show an embodiment of method 300 for sending an insulin delivery instructions and signature to an insulin delivery unit, accordingly to an embodiment. For example, insulin management application 152 sends an insulin delivery instruction and a signature to the insulin delivery unit 110.

At 302 of method 300, insulin management application 152 sends an authentication request to trusted authentication service 154. At 304, trusted authentication service 154 generates a confirmation prompt. At 306, trusted authentication service 154 asserts control over display hardware. At 308, trusted authentication service 154 sends a confirmation prompt to UI at display 156.

At 310, a confirmation prompt is displayed at the display 156 for user 160. At 312, user 160 provides an input response at the UI of display 156. The input response is then provided to trusted authentication service 154.

At 314, trusted authentication service 154 determines whether the input response is approved or denied. If approved, then trusted authentication service creates and sends a signature to insulin management application 152. Alternatively, at 316, if the input response is denied, then trusted authentication service 154 creates and sends an error message 316 to insulin management application 152. At 318, upon receiving a signature from trusted authentication service 154, insulin management application 152 sends delivery instructions to delivery controller 116 of insulin delivery unit 110 (as shown in FIG. 3B).

Referring now to FIG. 3B, at 320, delivery controller 116 requests authentication of the signature from authenticator 114. At 322, authenticator 114 verifies the signature using public key(s) in crypto-key storage 112 (e.g., key ROM 112). At 324, authenticator 114, sends indication to delivery controller 116 that the signature is either verified or not verified (based on the verification process using public key(s)).

At 326, if the instructions are verified by delivery controller 116, then delivery controller 116 adjusts the set points corresponding to the verified instructions. The commands/instructions are then sent to delivery mechanism 120.

At 328, if the instructions are not verified by delivery controller 116, then delivery controller does not adjusts the set points. The commands/instructions are then sent to delivery mechanism 120.

Figure 4A:
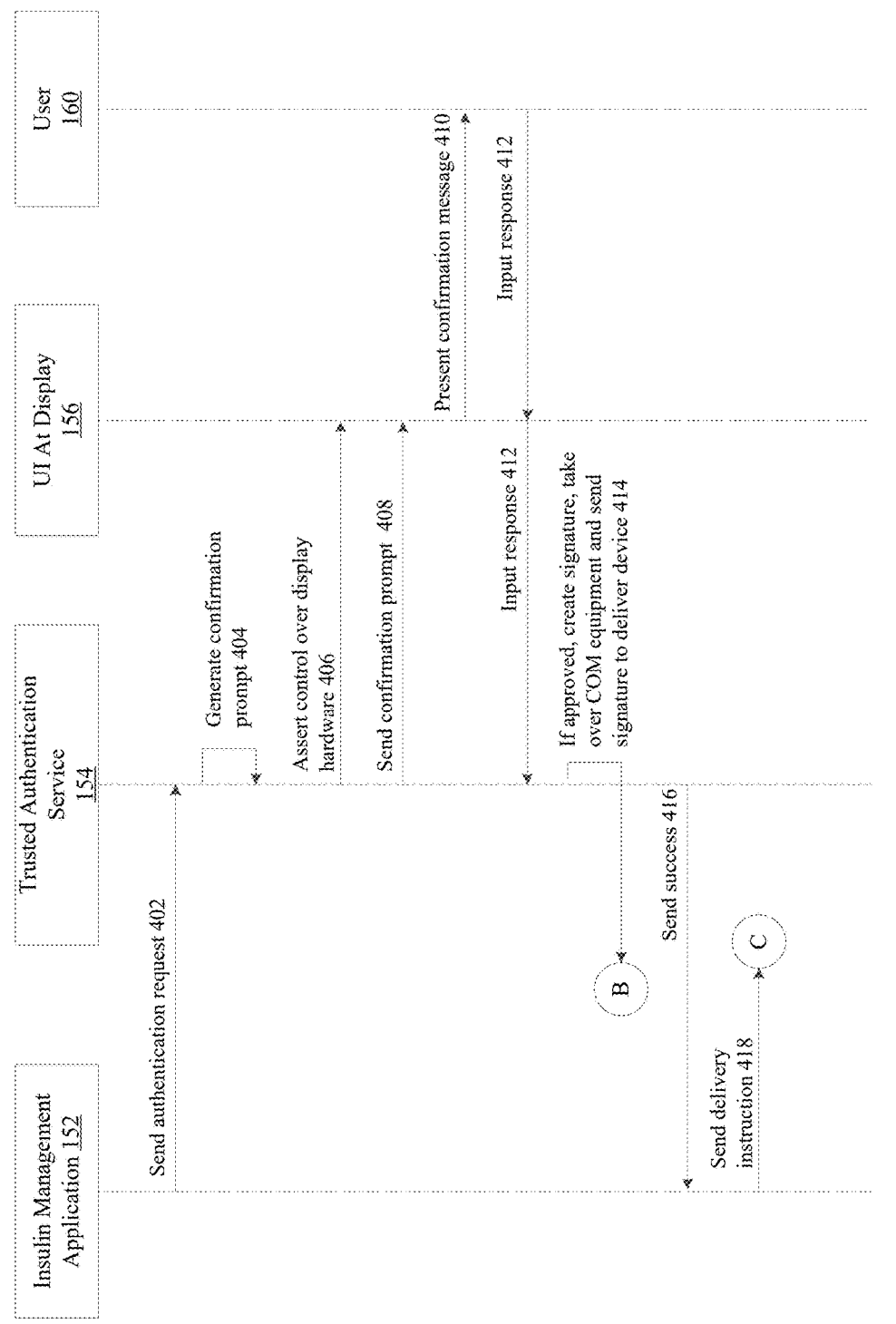
FIGS. 4A and 4B show an embodiment where the trusted authentication service sends the signature directly to the insulin delivery unit using a trusted communication process.
Figure 4B:
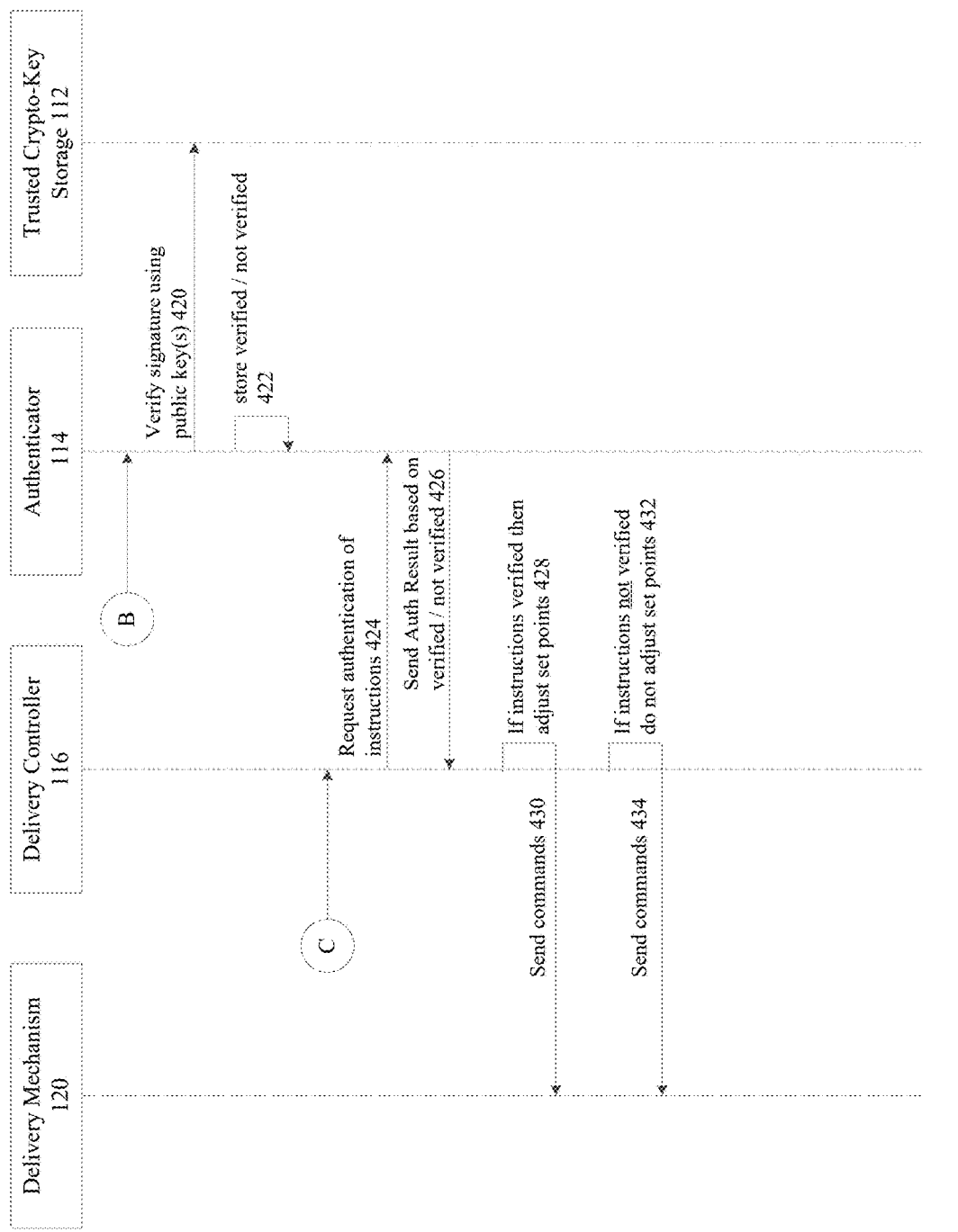

FIGS. 4A and 4B show an embodiment of method 400 for a trusted authentication service sending a signature. For example, trusted authentication service 154 sends the signature directly to the insulin delivery unit 110 using a trusted communication process whereby the trusted authentication service takes over communication equipment of the mobile computing device 150. In one embodiment, the trusted authentication service 154 may send the signature and the delivery instructions. In another embodiment, the trusted authentication service 154 may send the signature and an indication of the delivery instructions that the signature corresponds to, which were sent by the insulin management application 152.

At 402, insulin management application 152 sends an authentication request to trusted authentication service 154. At 404, trusted authentication service 154 generates a confirmation prompt. At 406, trusted authentication service 154 asserts control over display hardware. At 408, trusted authentication service 154 sends a confirmation prompt to UI at display 156.

At 410, a confirmation prompt is displayed at the display 156 for user 160. At 412, user 160 provides an input response at the UI of display 156. The input response is then provided to trusted authentication service 154.

At 414, trusted authentication service 154 determines whether the input response is approved. If approved, then trusted authentication service creates and sends a signature to a trusted authentication service. Additionally, the authentication service takes over communication (COM) equipment.

At 416, trusted authentication service 154 sends a success message to insulin management application. For example, if a confirmation is received via the controlled hardware inputs then the trusted authentication service signs a success message using a private key associated with the trusted authentication service, and sends the signed message to the medication therapy application. At 418, upon receiving a success message from trusted authentication service 154, insulin management application 152 sends delivery instructions to delivery controller 116 of insulin delivery unit 110 (as shown in FIG. 4B).

Now referring to FIG. 4B, at 420, authenticator 114 verifies a signature using public keys stored in key ROM 112. At 422, authenticator 114 stores a verified or not verified signature. At 424, delivery controller 116 requests authentication of instructions. At 426, authenticator 114 sends authentication results based on verified/not verified signature.

At 428, if instructions are verified, delivery controller 116 adjusts set points and sends commands to delivery mechanism 120 (at 430). Alternatively, at 432, if instructions are not verified, then delivery controller 116 does not adjust set points and sends commands to delivery mechanism 120 (at 434).

Figure 5A:
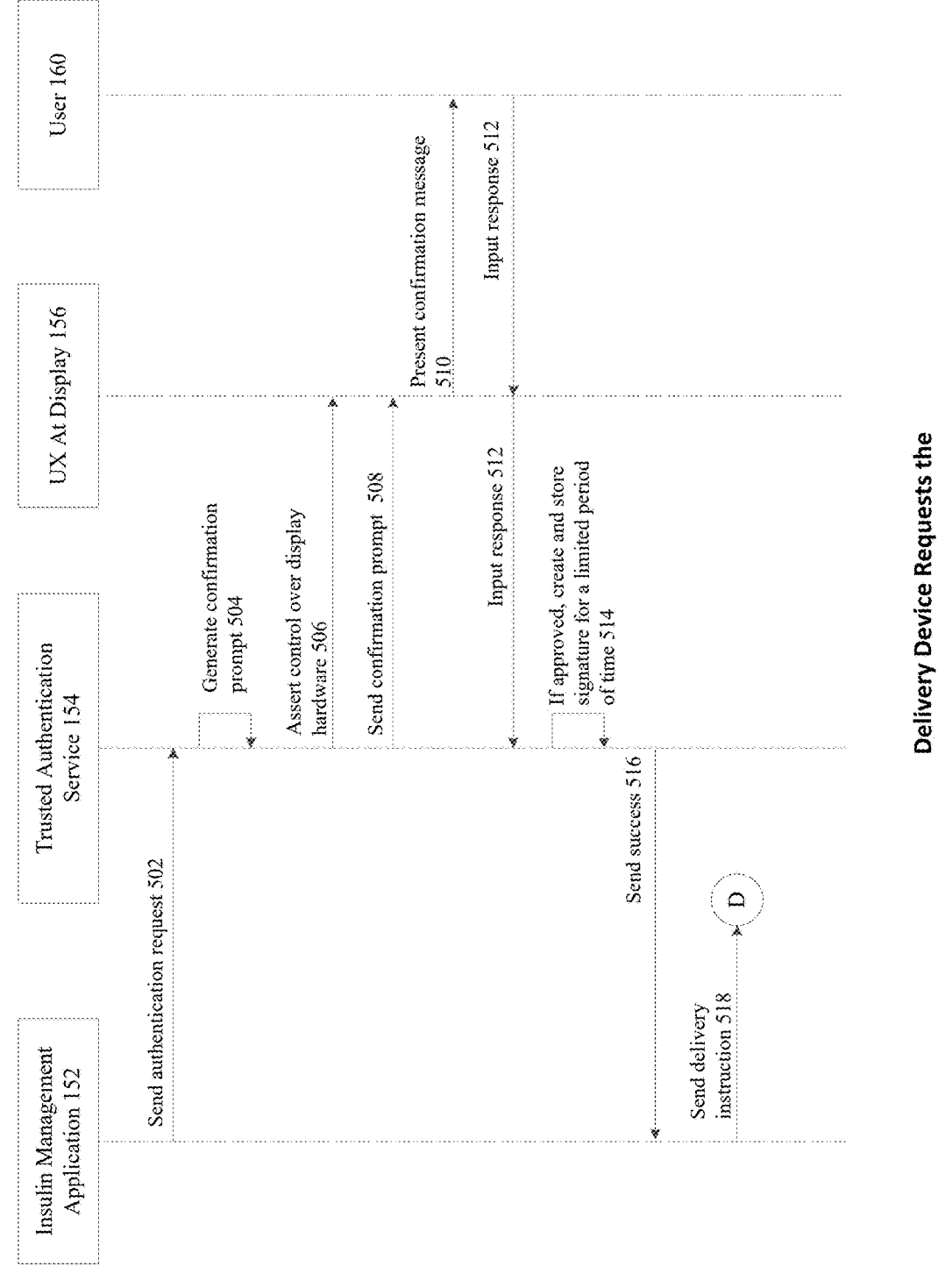
FIGS. 5A and 5B show an embodiment where the insulin delivery unit requests the signature from the trusted authentication service.
Figure 5B:
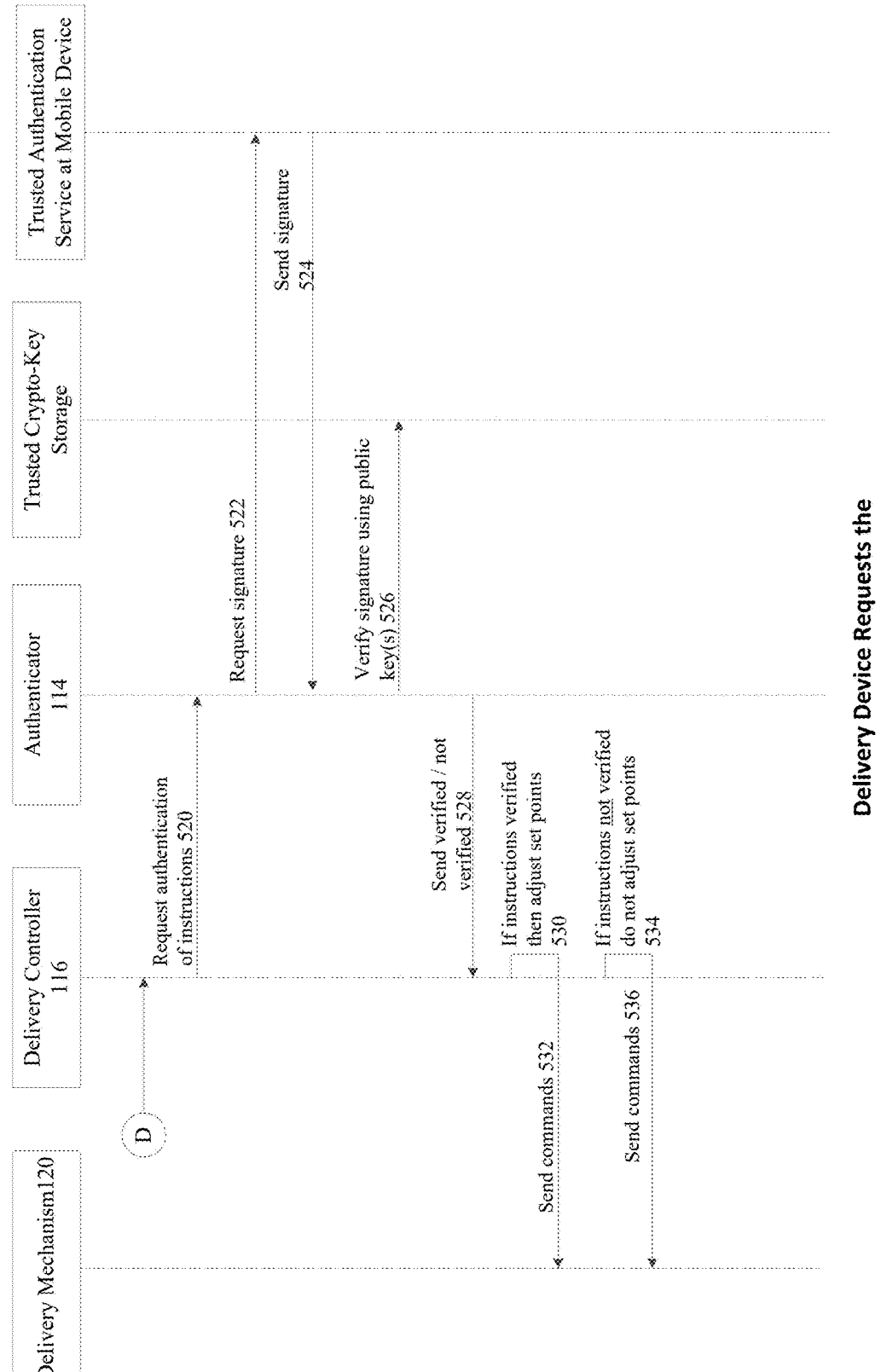

FIGS. 5A and 5B show an embodiment of method 500 for a delivery device requesting the signature from a mobile device. For example, the insulin delivery unit 110 requests the signature from the trusted authentication service 154 responsive to receiving a delivery instruction from the insulin management application 152. In one embodiment, the signature is stored by trusted authentication service 154 for a limited period of time. If the trusted authentication service 154 does not receiver a request for the signature before the time period expires then it will discard the signature. In one embodiment, the signature is stored by a trusted storage service (not shown) for a limited period of time. If the insulin management application 152 does not receive a request for the signature before the time expires then it instructs the trusted storage service to discard the signature.

At 502, insulin management application 152 sends an authentication request to trusted authentication service 154. At 504, trusted authentication service 154 generates a confirmation prompt. At 506, trusted authentication service 154 asserts control over display hardware. At 508, trusted authentication service 154 sends a confirmation prompt to UX at display 156.

At 510, a confirmation prompt is displayed at the display 156 for user 160. At 512, user 160 provides an input response at the UI of display 156. The input response is then provided to trusted authentication service 154.

At 514, trusted authentication service 154 determines whether the input response is approved. If approved, then trusted authentication service creates and stores a signature to a period of time.

At 516, trusted authentication service 154 sends a success message to insulin management application. At 518, upon receiving a success message from trusted authentication service 154, insulin management application 152 sends delivery instructions to delivery controller 116 of insulin delivery unit 110 (as shown in FIG. 5B).

Now referring to FIG. 5B, at 520, delivery controller requests authentication of instructions. At 522, authenticator requests signature from a trusted authentication service at a mobile device. At 524, a signature is sent to authenticator 114. At 526, authenticator verifies the signature using public key(s). At 528, authenticator 114 sends verified or not verified signature to delivery controller 116.

At 530, delivery controller 116 adjusts set point if instructions are verified and sends commands to delivery mechanism 120 (at 532). Alternatively, at 534 authenticator 114 verifies the signature using public key(s). At 534, delivery controller 116 adjusts set point if instructions are not verified and sends commands to delivery mechanism 120 (at 536).

FIG. 6 shows a confirmation process 600 executed in the TEE, according to embodiments of the disclosure. In operation 602, the medication therapy application requests a REE authentication instance for the REE authentication service via the REE API. A dedication instance is not required, but it may provide additional isolation from other processes executing at the TEE. In operation 604, the REE API sets up a REE authentication instance with the trusted authentication service executing in the TEE. In operation 606, the trusted authentication services creates a prompt based on the delivery instructions or using text provided by the insulin therapy application, such that the prompt presents the insulin delivery instructions in a form understandable by a user. In operation 608, the trusted authentication services takes control of the hardware display and hardware inputs and presents the prompt to the user at the hardware display. In operation 610, the trusted authentication service receives user input at the controlled hardware inputs. In operation 612, if a confirmation is received via the controlled hardware inputs then the trusted authentication service signs a success message using a private key associated with the trusted authentication service, and sends the signed message to the medication therapy application. In operation 614, if no confirmation is received using the controlled hardware input then the trusted authentication service sends an error message to the medication therapy application.

Figure 7:
FIG. 7 shows the insulin therapy system in use by a user, according to embodiments of the disclosure.

FIG. 7 shows the insulin therapy system 700 in use by a patient/user, according to embodiments of the disclosure. System 700 may include a pump assembly 715 for insulin and a continuous glucose monitor 750. As shown, the continuous glucose monitor 750 is in wireless communication with pump assembly 715. In some cases, a continuous glucose monitor can be in wired communication with pump assembly 715. In some cases not shown, a continuous glucose monitor can be incorporated into an insulin pump assembly. As shown, pump assembly 715 can include a reusable pump controller 720 that forms part of the pump assembly 715. In some cases, reusable pump controller 720 is adapted to determine one or more basal delivery rates. In some cases, continuous glucose monitor 750 can act as a controller adapted to communicate basal delivery rates to pump assembly 715.

Pump assembly 715, as shown, can include reusable pump controller 720 and a disposable pump 730, which can contain a reservoir for retaining insulin. A drive system for pushing insulin out of the reservoir can be included in either the disposable pump 730 or the reusable pump controller 720 in a controller housing 722. Reusable pump controller 720 can include a wireless communication device 747, which can be adapted to communicate with a wireless communication device 754 of continuous glucose monitor 750 and other diabetes devices in the system, such as those discussed below. In some cases, pump assembly 715 can be sized to fit within a palm of a hand 705. Pump assembly 715 can include an infusion set 780. Infusion set 780 can include a flexible tube 782 that extends from the disposable pump 730 to a subcutaneous cannula 149 that may be retained by a skin adhesive patch (not shown) that secures the subcutaneous cannula 784 to the infusion site. The skin adhesive patch can retain the subcutaneous cannula 784 in fluid communication with the tissue or vasculature of the PWD so that the medicine dispensed through flexible tube 782 passes through the subcutaneous cannula 784 and into the PWD's body. The cap device 736 can provide fluid communication between an output end of an insulin cartridge (not shown) and flexible tube 782 of infusion set 780. Although pump assembly 715 is depicted as a two-part insulin pump, one piece insulin pumps are also contemplated. Additionally, insulin pump assemblies used in methods and systems provided herein can alternatively be a patch pump.

Continuous glucose monitor 750 (e.g., a glucose sensor) can include a housing 752, a wireless communication device 754, and a sensor shaft 756. The wireless communication device 754 can be contained within the housing 752 and the sensor shaft 756 can extend outward from the housing 752. In use, the sensor shaft 756 can penetrate the skin 786 of a user to make measurements indicative of the PWD's blood glucose level or the like. In some cases, the sensor shaft 756 can measure glucose or another analyte in interstitial fluid or in another fluid and correlate that to blood glucose levels. In response to the measurements made by the sensor shaft 756, the continuous glucose monitor 750 can employ the wireless communication device 754 to transmit data to a corresponding wireless communication device 747 housed in the pump assembly 715. In some cases, the continuous glucose monitor 750 may include a circuit that permits sensor signals (e.g., data from the sensor shaft 756) to be communicated to the wireless communication device 754. The wireless communication device 754 can transfer the collected data to reusable pump controller 720 (e.g., by wireless communication to the wireless communication device 747). Additionally or alternatively, the system 700 may include another glucose monitoring device that may utilize any of a variety of methods of obtaining information indicative of a PWD's blood glucose levels and transferring that information to reusable pump controller 720. For example, an alternative monitoring device may employ a micropore system in which a laser porator creates tiny holes in the uppermost layer of a PWD's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. In other examples, the monitoring device can include detect glucose levels using equilibrium fluorescence detectors (e.g., sensors including a diboronic acid receptor attached to a fluorophore). Furthermore, it should be understood that in some alternative implementations, continuous glucose monitor 750 can be in communication with reusable pump controller 720 or another computing device via a wired connection. In some cases, continuous glucose monitor 750 can be adapted to provide blood glucose measurements for a PWD when in use for the PWD at regular or irregular time intervals. In some cases, continuous glucose monitor 750 can detect blood glucose measurements at least every thirty minutes, at least every fifteen minutes, at least every ten minutes, at least every five minutes, or about every minute. In some cases, continuous glucose monitor 750 can itself determine a basal delivery rate using methods provided herein and communicate that basal rate to the pump assembly 715. In some cases, continuous glucose monitor 750 can transmit blood glucose measurement data to reusable pump controller 720 and reusable pump controller 720 can use methods provided herein to determine a basal delivery rate. In some cases, a remote controller can receive glucose data from continuous glucose monitor 750, determine a basal delivery rate using methods provided herein, and communicate the basal rate to pump assembly 715.

Diabetes management system or insulin therapy system 700 (system 700) may optionally include a blood glucose meter 770 (e.g., a glucose sensor). In some cases, blood glucose meter 770 can be in wireless communication with reusable pump controller 720. Blood glucose meter 770 can take a blood glucose measurement using one or more test strips (e.g., blood test strips). A test strip can be inserted into a strip reader portion of the blood glucose meter 770 and then receive the PWD's blood to determine a blood glucose level for the PWD. In some cases, the blood glucose meter 770 is configured to analyze the characteristics of the PWD's blood and communicate (e.g., via a BLUETOOTH® wireless communication connection) the information to reusable pump controller 720. In some cases, a user can manually input a glucose meter reading. The blood glucose meter 770 can be manually operated by a user and may include an output subsystem (e.g., display, speaker) that can provide the user with blood glucose readings that can be subsequently entered into the controller or user interface to collect the data from an unconnected BGM into the system. The blood glucose meter 770 may be configured to communicate data (e.g., blood glucose readings) obtained to reusable pump controller 720 and/or other devices, such as the mobile computing device 760 (e.g., a control device). Such communication can be over a wired and/or wireless connection, and the data can be used by system 700 for a number of functions (e.g., calibrating the continuous glucose monitor 750, confirming a reading from the continuous glucose monitor 750, determining a more accurate blood glucose reading for a bolus calculation, detecting a blood glucose level when the continuous glucose monitor 750 is malfunctioning).

In some cases, the system 700 can further include a mobile computing device 760 that can communicate with the reusable pump controller 720 through a wireless and/or wired connection with the reusable pump controller 720 (e.g., via a BLUETOOTH® wireless communication connection or a near-field communication connection). In some cases, the mobile computing device 760 communicates wirelessly with other diabetes devices of system 700. The mobile computing device 760 can be any of a variety of appropriate computing devices, such as a smartphone, a tablet computing device, a wearable computing device, a smartwatch, a fitness tracker, a laptop computer, a desktop computer, and/or other appropriate computing devices. In some cases (for example, where the reusable pump controller 720 does not determine a basal delivery rate), the mobile computing device 760 can receive and log data from other elements of the system 700 and determine basal delivery rates using methods provided herein. In some cases, a user can input relevant data into the mobile computing device 760. In some cases, the mobile computing device 760 can be used to transfer data from the reusable pump controller 720 to another computing device (e.g., a back-end server or cloud-based device). In some cases, one or more methods provided herein can be performed or partially performed by the other computing device. In some cases, the mobile computing device 760 provides a user interface (e.g., graphical user interface (GUI), speech-based user interface, motion-controlled user interface) through which users can provide information to control operation of the reusable pump controller 720 and the system 700. For example, the mobile computing device 760 can be a mobile computing device running a mobile app that communicates with reusable pump controller 720 over short-range wireless connections (e.g., BLUETOOTH® connection, Wi-Fi Direct connection, near-field communication connection, etc.) to provide status information for the system 700 and allow a user to control operation of the system 700 (e.g., toggle between delivery modes, adjust settings, log food intake, change a fear of hypoglycemia index (FHI), confirm/modify/cancel bolus dosages, and the like).

Optionally, system 700 may include a bolus administering device 790 (e.g., a syringe, an insulin pen, a smart syringe with device communication capabilities, or the like) through which bolus dosages can be manually administered to a PWD. In some cases, a suggested dosage for a bolus to be administered using the bolus administering device 790 can be output to a user via the user interface of reusable pump controller 720 and/or the user interface of the mobile computing device 760. In some cases, the bolus administering device 790 can communicate through a wired and/or wireless connection with reusable pump controller 720 and/or the mobile computing device 760. In some cases, system 700 can allow users to input insulin deliveries made using a syringe or insulin pen.

In some cases, methods and systems of treating diabetes can include the use of an pump assembly 715 (e.g., an "insulin pump assembly"), which can be used to deliver both a continuous (or semi-continuous) supply of quick acting insulin at a personalized BR and to delivery boluses of the quick acting insulin to make corrections for elevated blood glucose levels or to address consumed carbohydrates. In some cases, methods and systems of treating diabetes can include the use of a continuous glucose monitor 750 (CGM) that can communicate blood glucose data to a controller such as the mobile computing device 760 and/or the reusable pump controller 720 that can automate insulin delivery dynamically to address current or anticipated high or low blood glucose levels. In some cases, methods and systems provided herein can make adjustments to therapeutic parameters based upon the automated insulin deliveries determined using continuous (or semi-continuous) blood glucose data.

In some cases, methods and systems of treating diabetes can include the use of multiple daily injections (MDI) of different types of insulin. For example, MDI can include the injection of long acting insulin at least once a day to cover a baseline insulin requirement and the injection of a quick acting insulin to make corrections or to address consumed carbohydrates.

In some embodiments, the system 700 may include a bolus administering device 790 (e.g., a syringe, an insulin pen, a smart syringe with device communication capabilities using quick acting insulin, or the like) through which bolus dosages can be manually administered to a PWD. As illustrated in FIG. 7, such a bolus administering device may be referred to as an injection based delivery device. In some cases, a suggested dosage for a bolus to be administered using the bolus administering device 790 can be output to a user via the user interface of reusable pump controller 720 and/or the user interface of the mobile computing device 760. In some cases, the bolus administering device 790 can communicate through a wired and/or wireless connection with reusable pump controller 720 and/or the mobile computing device 760. In some cases, system 700 can allow users to input insulin deliveries made using a syringe or insulin pen.

In some embodiments, the system 700 may include a basal administering device 792 (e.g., a syringe, an insulin pen, a smart syringe with device communication capabilities using long acting insulin, or the like) through which basal insulin can be manually administered to a PWD, such as a once per day dose or a twice per day dose. As illustrated in FIG. 7, such a basal administering device may be referred to as an injection based delivery device. In some cases, the amount of basal insulin for a given dose may be determined by the mobile computing device 760. For example, the mobile computing device 760 may display an amount of insulin to be delivered as a daily basal dose. Additionally or alternatively, if the basal administering device 792 includes communication capabilities, the mobile computing device 760 may transmit a message to the basal administering device 792 indicating the amount of basal insulin to be delivered in the dose.

Figure 8A:
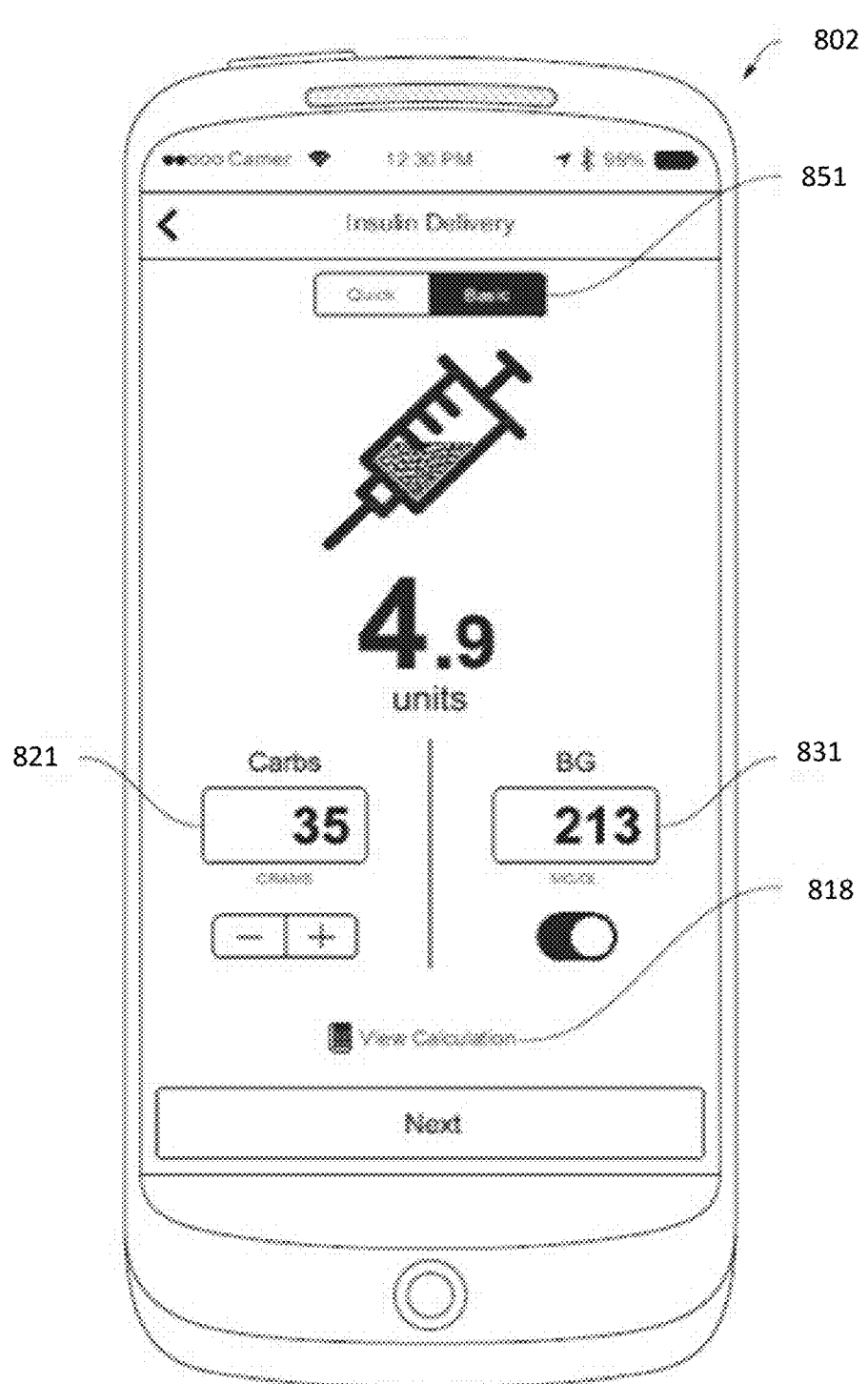
Figure 8B:
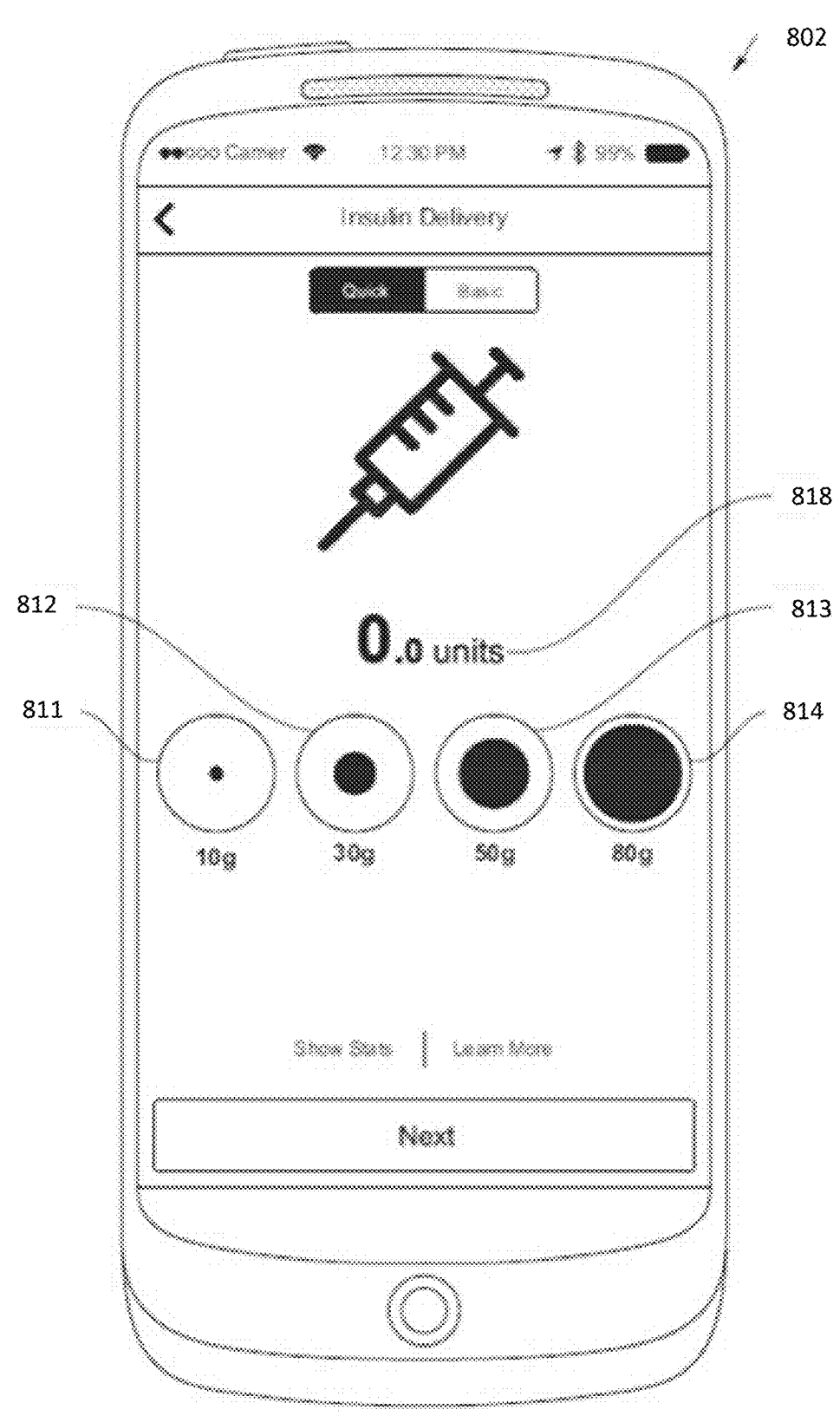
Figure 8C:
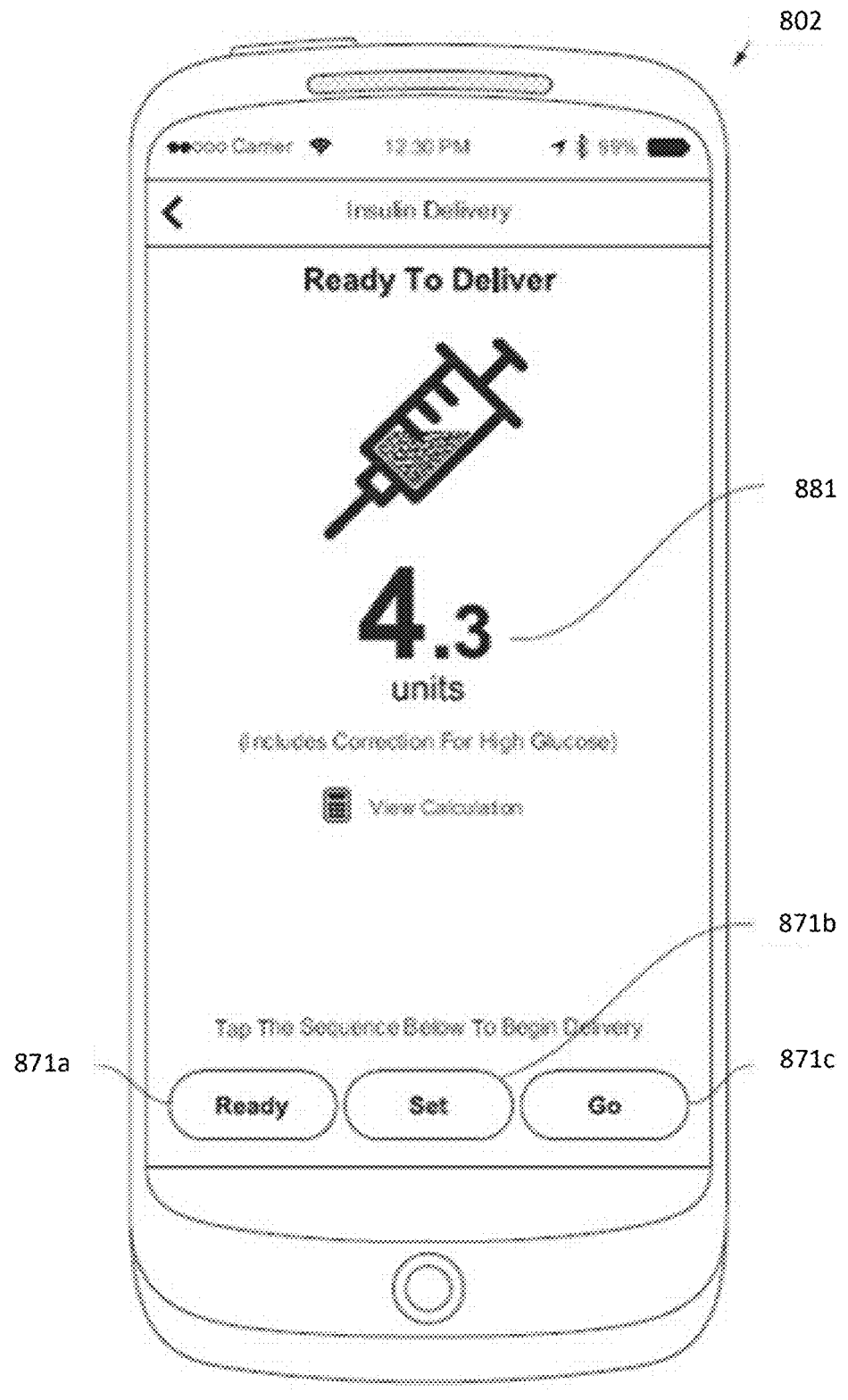

FIGS. 8A-8D show exemplary user interfaces for an insulin therapy application, displayed on device 802 that may be used to calculate a bolus, according to embodiments of the disclosure. In FIG. 8A, a user might indicate the size of a meal, which can be represented as a number of grams of carbohydrates, that the user intends to eat in field 821 in order to request that the system calculate a bolus. Additionally, a user can indicate the current estimated blood glucose (BG) value in field 831. In some cases, field 831 can auto populate based on data received from continuous glucose monitor 750 and/or blood glucose meter 770 or any other suitable glucose sensor. Based on that data, the bolus calculator can indicate a recommended dosage of insulin (in units), and the user can view how that was calculated by viewing the calculation 818. By using toggle switch 851, a user may use a different user interface that provides the user with predetermined meal sizes (811-814) via the user interface, as shown in FIG. 8B. By pressing "NEXT," the user can be presented with a screen that indicates that device 802 is about to deliver the recommended bolus 881. If the user presses on the recommended bolus 881, the user can adjust this number based on the user's specific preference. By pressing ready 871*a*, set 871*b*, go 871*c* (or other suitable user interaction to indicate a desire to deliver the bolus), the smartphone will send a signal to the TEE to confirm the bolus instruction. FIG. 8D, the TEE overrides the user interface of the smartphone and presents the user with a confirmation screen 880 or popup of the bolus instruction, including the units of insulin to be delivered, so that the user can confirm the intent to deliver that amount of insulin.

Figure 9A:
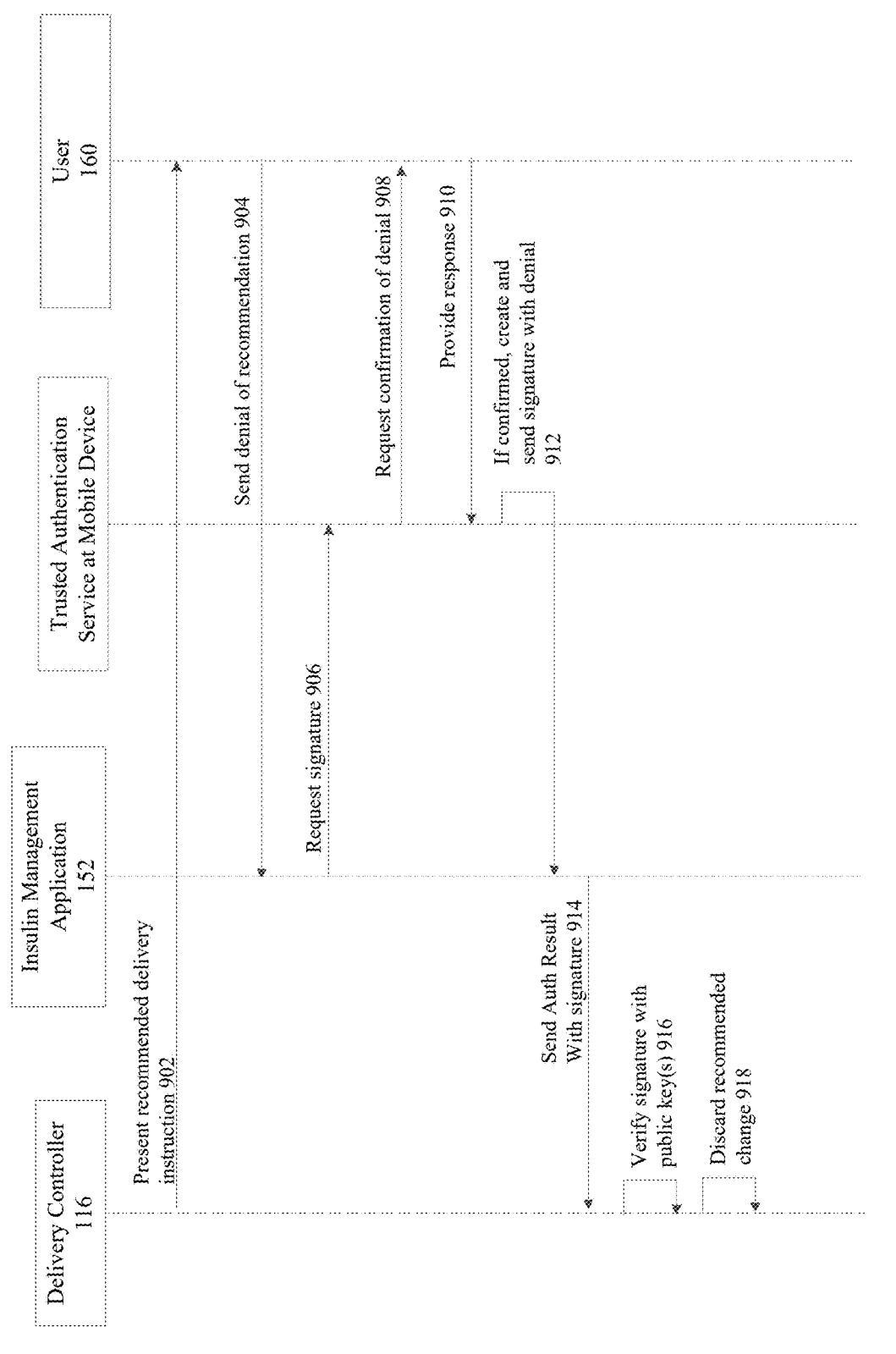
FIG. 9A shows a use case where methods, devices, and systems provided herein may only require the TEE to confirm the delivery instruction if the user elects to deliver a bolus other than a recommended bolus, according to an embodiment of the disclosure.

FIG. 9A shows a use case where methods, devices, and systems provided herein may only require the TEE to confirm the delivery instruction if the user elects to deliver a bolus other than a recommended bolus. FIG. 9A depicts a method 900 for a TEE to confirm the delivery instruction if the user elects to deliver a bolus other than a recommended bolus. For example, a recommended bolus might not be calculated by the insulin therapy application, but might instead be calculated by the delivery controller at the insulin delivery unit, and a user interaction with the screen of FIG. 8C to deliver the recommended bolus might provide an instruction to the insulin pump to deliver the recommended bolus. In some cases, the use of the TEE to confirm a user instruction to bolus might only be triggered if the amount of the bolus exceeds a threshold or if it is close in time to another bolus event or if the system determines that the bolus is unsafe or unusual.

At 902, delivery controller 116 presents recommended delivery instructions to user 160. At 904, a denial of the recommendation is sent to insulin management application 152. At 906, insulin management application 152 requests a signature from a trusted authentication service at a mobile device. At 908, the trusted authentication service requests confirmation of the denial. At 910, a response of the confirmed denial is received at the trusted authentication service. At 912, upon confirmation, a signature is created and sent with the denial to insulin management application 152. At 914, authentication results with a signature are sent to delivery controller 116. At 916, delivery controller 116 verifies the signature with public key(s). At 918, delivery controller 116 discards the recommended change.

FIG. 9B shows an example of a recommendation 950 provided by the insulin delivery unit to the mobile computing device to bolus in response to a trend toward higher blood glucose levels that may trigger the confirmation process shown in FIG. 9A.

Figure 10:
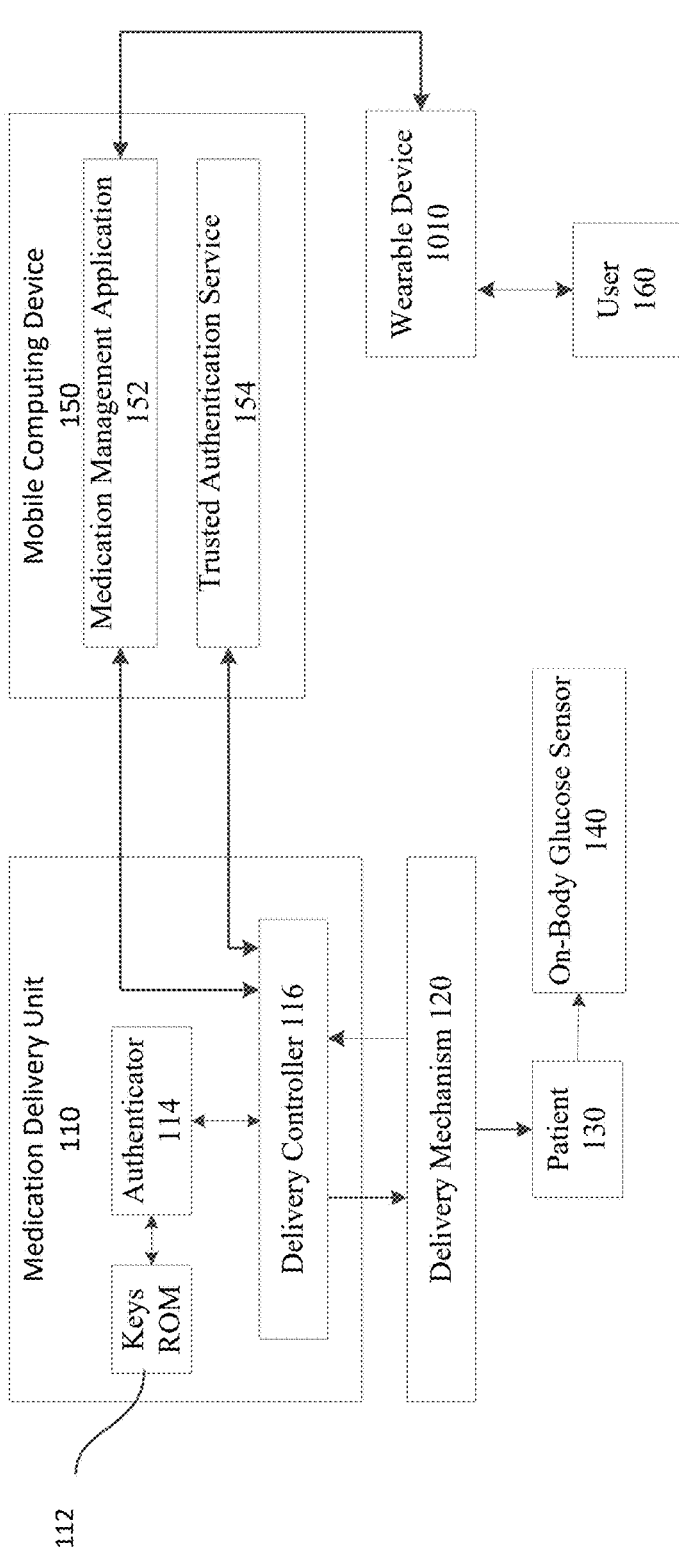
FIG. 10 shows a therapy management system where the user interfaces with a wearable device is configured to be taken over by the trusted authentication service, and permit a user to provide confirmation of a bolus dose, according to an embodiment of the disclosure.

FIG. 10 shows a therapy management system 1000 (similar to insulin therapy system 100) where the user interfaces with a wearable device 1010 is configured to be taken over by the trusted authentication service, and permit a user to provide confirmation of a bolus dose, according to an embodiment of the disclosure.

Figure 11:
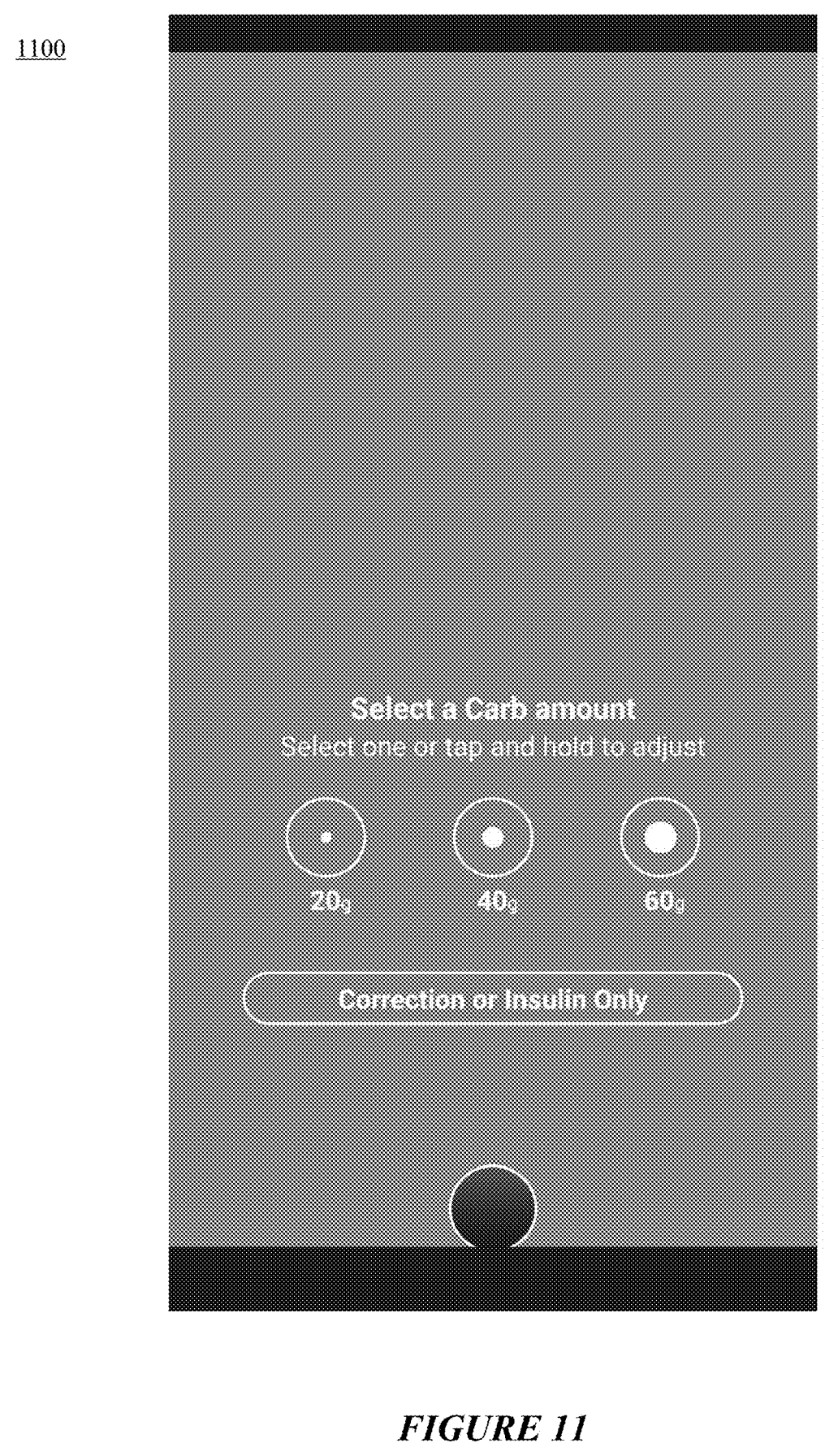

FIG. 11 shows an example of a user interface 1100 where the user, instead of entering the amount of carbs selects a meal or carbohydrate amount associated with a meal-type that the user entered, according to an embodiment of the disclosure.

This disclosure also describes, generally, methods to increase confidence that a user-specified parameter was confirmed by a user and, indeed, it was a user action that confirmed the user-specified parameter. The embodiments computing architecture, including those shown in FIG. 2 may be configured to implement such methods. A user-specified parameter may be any parameter that may be used by, or affect a parameter used by, a medication therapy application to control medication delivery or make recommendations related to medication delivery or medication therapy, more generally, (e.g., a medication therapy recommendation, or, in the case of insulin therapy, an insulin therapy recommendation). Examples of user-specified parameters include carbohydrate intake, exercise, sleep, changes of dosing information for a previous dose (e.g., changing a previous dose from rapid acting to long acting insulin to correct an error). User-specified parameters may also include physiological parameters, such as insulin sensitivity, age, weight, gender, etc.

Figure 12A:
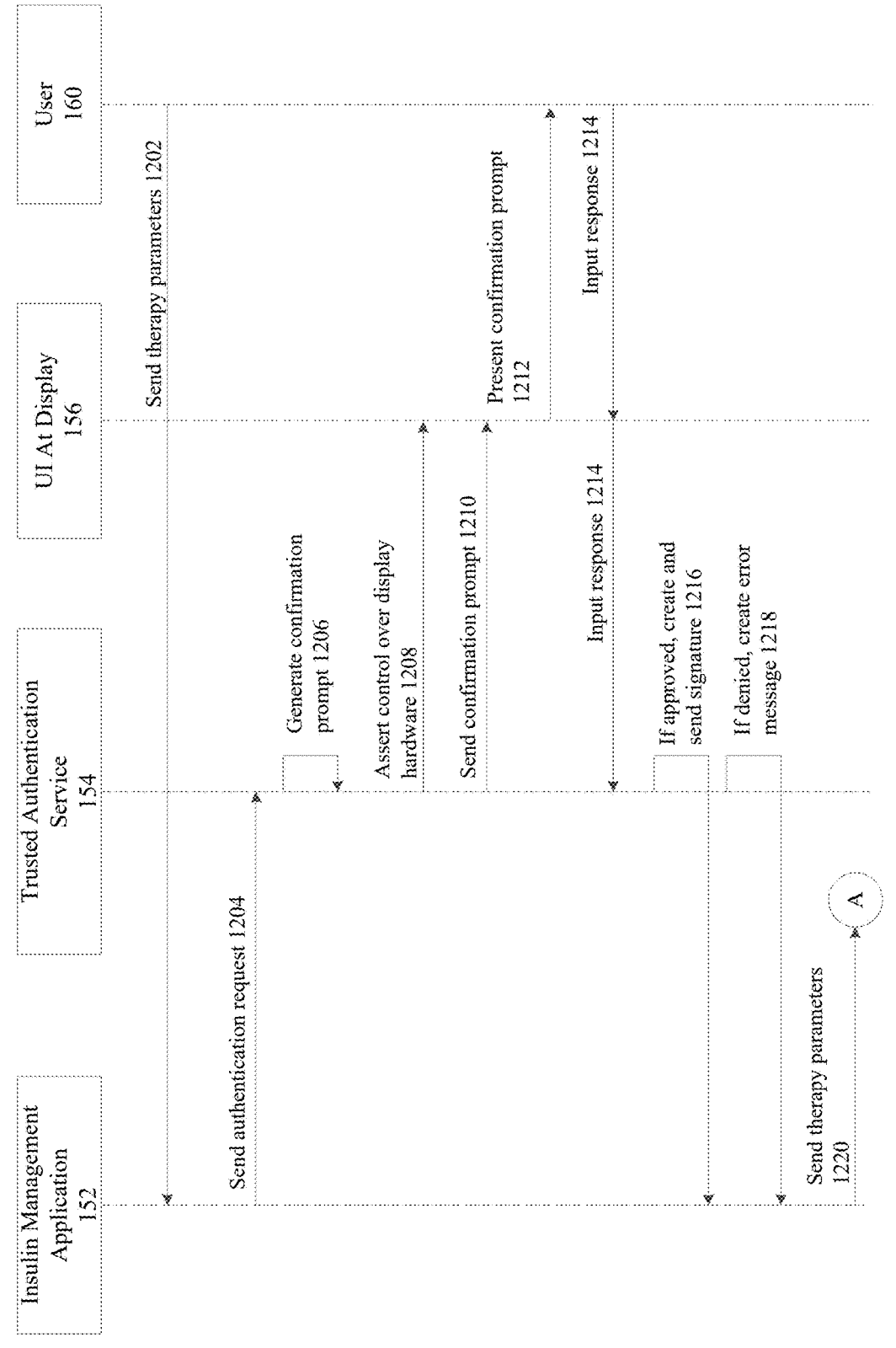
FIGS. 12A and 12B show an embodiment where a trusted authentication service is used to confirm user-specified parameters that would affect medication therapy or medication delivery recommendations, according to an embodiment of the disclosure.
Figure 12B:

FIGS. 12A and 12B show a method 1200 where a trusted authentication service is used to confirm user-specified parameters that would affect medication therapy or medication delivery recommendations. For example, a user-specified parameter may correspond to a change to physiological parameters such as a patient's insulin sensitivity, age, weight, health (e.g., the patient is sick), etc. By way of further example, a user-specified parameter may correspond to a change to a therapy parameter such as a change to a basal rate of insulin.

In one embodiment, the insulin delivery unit may be a closed loop or open loop insulin pump, but in other embodiments it may be other insulin delivery devices that include an output sub-system connected to a display and/or indicators (e.g., LEDs, audio output, etc.), that enable them to make insulin delivery and, more generally, insulin therapy, recommendations, such as a smart insulin pen, a reusable cap adapted to attach to an insulin pen, or a smart accessory that is adapted to attach to an insulin pen or insulin inhaler. In various embodiments, a reusable cap may be reusable, for example, because it is adapted to be releasably attached to an insulin pen and/or associated with an insulin pen and then associated with a different insulin pen.

At 1202, therapy parameters are sent to insulin management application 152. At 1204, insulin management application 152 sends an authentication request to trusted authentication service 154. At 1206, trusted authentication service 154 generates a confirmation prompt. At 1208, trusted authentication service 154 asserts control over display hardware. At 1210, trusted authentication service 154 sends a confirmation prompt to UI at display 156.

At 1212, a confirmation prompt is displayed at the display 156 for user 160. At 1214, user 160 provides an input response at the UI of display 156. The input response is then provided to trusted authentication service 154.

At 1216, trusted authentication service 154 determines whether the input response is approved. If approved, then trusted authentication service creates and sends a signature to insulin management application 152. Alternatively, at 1218, if the input response is denied, then trusted authentication service 154 creates and sends an error message to insulin management application 152. At 1220, upon receiving a signature from trusted authentication service 154, insulin management application 152 sends therapy parameters to delivery controller 116 of insulin delivery unit 110 (as shown in FIG. 12B).

Referring now to FIG. 12B, at 1222, delivery controller 116 requests authentication of the signature from authenticator 114. At 322, authenticator 114 verifies the signature using public key(s) in crypto-key storage 112 (e.g., key ROM 112). At 1224, authenticator 114 retrieves private key(s) from key ROM 112. At 1226, authenticator 114 compares the keys. At 1228, authenticator sends the results to delivery controller 116.

At 1230, if the instructions are verified by delivery controller 116, then delivery controller 116 adjusts the set points corresponding to the verified instructions. At 1232, if the instructions are not verified by delivery controller 116, then delivery controller does not adjusts the set points.

The embodiments described herein may include the use of a special-purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general-purpose or special-purpose computer. Special-purpose computer is intended to be interpreted broadly and encompasses embedded systems, microcontrollers, application specific integrated circuits, digital signal processors, and general-purpose computers programmed for specific purposes. Segments (e.g., code segment or data segment) may refer to a portion (e.g., address) of memory, virtual memory, or an object file.

By way of example, and not limitation, such computer-readable media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid-state memory devices), or any other storage medium which may be used to carry or store desired program code in the form of computer-executable instructions or data structures and which may be accessed by a general-purpose or special-purpose computer. Combinations of the above may be included within the scope of computer-readable media.

Computer-executable instructions comprise, for example, instructions and data which cause a general-purpose computer, special-purpose computer, or special-purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Any ranges expressed herein (including in the claims) are considered to be given their broadest possible interpretation. For example, unless explicitly mentioned otherwise, ranges are to include their endpoints (e.g., a range of "between X and Y" would include X and Y). Additionally, ranges described using the terms "approximately" or "about" are to be understood to be given their broadest meaning consistent with the understanding of those skilled in the art. Additionally, the terms "approximately" or "substantially" include anything within 10%, or 5%, or within manufacturing or typical tolerances.

Any characterization in this disclosure of something as "typical," "conventional," or "known" does not necessarily mean that it is disclosed in the prior art or that the discussed aspects are appreciated in the prior art. Nor does it necessarily mean that, in the relevant field, it is widely known, well-understood, or routinely used.

The features of the various embodiments described herein are not mutually exclusive and can exist in various combinations and permutations, even if such combinations or permutations are not expressly described herein, without departing from the scope of the disclosure. In fact, variations, modifications, and other implementations of what is described herein will occur to one of ordinary skill in the art without departing from the scope of the disclosure. As such, the invention is not to be defined only by the preceding illustrative description, but only by the claims which follow, and legal equivalents thereof.

We claim:

1. A mobile computing device for providing medication therapy recommendations, comprising:

a secure execution environment having at least one trusted authentication service that executes therein, the secure execution environment including a secure kernel configured to handle commands and access isolated hardware resources including a processor, memory and device I/O, wherein the at least one trusted authentication service is configured to establish a secure user interaction process at the mobile computing device via a rich operating system different than a mobile operating system of the mobile computing device;

a normal execution environment having a medication therapy application executed therein via the mobile operating system, wherein the medication therapy application is configured to:

determine at least one medication delivery instruction;

responsive to determining at least one medication delivery instruction, send a request for a trusted user confirmation to the at least one trusted authentication service of the mobile computing device, wherein, responsive to receiving the request for the trusted user confirmation, the at least one trusted authentication service is configured to:

initiate the secure user interaction process, the process configured to:

prevent the normal execution environment from receiving, and allow the secure execution environment to receive, a user input via a user interface of the mobile computing device;

while the normal execution environment is prevented from receiving a user input via the user interface, present a request, via the user interface, for a user interaction with the mobile device as a trusted user confirmation that confirms the at least one medication delivery instruction; and responsive to receiving the trusted user confirmation, generate and provide a signature and success message to the medication therapy application, wherein, responsive to receiving the signature and success message, the medication therapy application is configured to provide certified medication delivery instructions to a medication delivery unit;

wherein, responsive to receiving the certified medication delivery instructions, the medication delivery unit is configured to:

authenticate the signature using one or more cryptographic keys stored on the medication delivery unit; and provide one or more delivery commands to a medication delivery mechanism responsive to successful authentication of the signature.

2. The mobile computing device of claim 1, wherein the medication delivery unit comprises an insulin pump.

3. The mobile computing device of claim 1, wherein the medication delivery unit comprises an insulin pen.

4. The mobile computing device of claim 1, wherein the medication delivery unit comprises a reusable insulin pen.

5. The mobile computing device of claim 1, wherein the secure user interaction process at the mobile computing device comprises displaying insulin dosing amounts at the graphical user interface of the mobile computing device.

6. The mobile computing device of claim 1, wherein the requested user interaction is manipulation of hardware inputs.

7. The mobile computing device of claim 1, wherein the requested user interaction is receiving biometric data from a user.

8. The mobile computing device of claim 1, wherein the medication therapy application is configured to request the trusted user confirmation in response to a change to a recommended insulin delivery instruction.

9. An insulin delivery system comprising:

a mobile computing device comprising:

a medication therapy application executed via a mobile operating system of the mobile computing device, the medication therapy application configured to, responsive to a determined at least one insulin therapy instruction, send a request for a trusted user confirmation to a trusted authentication service that executes in a secure execution environment including a secure kernel configured to handle commands and access isolated hardware resources including a processor, memory and device I/O, of the mobile computing device, the at least one trusted authentication service executed via a rich operating system different than the mobile operating system, wherein the at least one trusted authentication service is configured to:

responsive to the request for a trusted user confirmation, initiate a secure user interaction process configured to:

prevent the mobile operating system from receiving, and allow the rich operating system to receive, a user input via a user interface of the mobile computing device;

while the mobile operating system is prevented from receiving a user input via the user interface of the mobile computing device, present a request, via the user interface, for a user confirmation as a trusted user confirmation that confirms the at least one insulin therapy instruction;

responsive to receiving the trusted user confirmation, generate and provide a signature and success message to the medication therapy application;

an insulin delivery controller that is configured to receive the determined at least one insulin therapy instruction from the insulin therapy application and request authentication of the signature responsive to the success message, a signature authenticator configured to receive the authentication request from the insulin delivery controller and authenticate the signature responsive to a stored cryptographic key, and a delivery mechanism configured to deliver insulin according to an insulin delivery instruction responsive to successful authentication of the signature.

10. The insulin delivery system of claim 9, wherein the insulin delivery controller is further configured to receive glucose levels from a glucose sensor.

11. The insulin delivery system of claim 9, wherein the signature authenticator is further configured to authenticate the signature using one or more public keys stored on an insulin delivery unit different than the mobile computing device.

12. The insulin delivery system of claim 9, wherein the signature authenticator is further configured to send indication to the insulin delivery controller that the signature is either verified or not verified based on one or more public keys.

13. The insulin delivery system of claim 9, further comprising a crypto-key storage for storing one or more public keys.

14. An insulin pen comprising:

an insulin delivery controller configured to receive user-specified parameters from a mobile computing device and use the user-specified parameters to make insulin therapy recommendations, and wherein the insulin pen is configured to use the user-specified parameters responsive to a signature received from the mobile computing device, wherein the signature is indicative that the user-specified parameters were confirmed using a secure user interaction process at the mobile computing device, the secure user interaction process being initiated by a trusted authentication service that executes in a secure execution environment including a secure kernel configured to handle commands and access isolated hardware resources including a processor, memory and device I/O, the trusted authentication service executed via a rich operating system of the mobile computing device different than a mobile operating system of the mobile computing device responsive to a request for a trusted user confirmation from a medication therapy application executed via the mobile operating system of the mobile device, the secure user interaction process comprising the trusted authentication service:

initiating a secure user interaction process; and using the secure interaction process:

prevent the mobile operating system from receiving, and allow the rich operating system to receive, a user input via a user interface of the mobile computing device;

while the mobile operating system is prevented from receiving a user input from the user interface of the mobile computing device, present a request, via the user interface, for a trusted user confirmation of the user specified parameters; and responsive to receiving the trusted user confirmation, generating and providing the signature and success message to the medication therapy application.

15. The insulin pen of claim 14, further comprising:

a read only memory (ROM) storing one or more public keys; and a signature authenticator configured to authenticate the signature using the one or more public keys.

16. A reusable insulin pen cap associated with at least one insulin pen comprising:

an insulin delivery controller configured to receive user-specified parameters from a mobile computing device and use the user-specified parameters to make insulin therapy recommendations, wherein a reusable pen cap is configured to use the user-specified parameters responsive to a signature received from the mobile computing device, wherein the signature is indicative that the user-specified parameters were confirmed using a secure user interaction process at the mobile computing device, the secure user interaction process being initiated by a trusted authentication service that executes in a secure execution environment including a secure kernel configured to handle commands and access isolated hardware resources including a processor, memory and device I/O, the trusted authentication service executed via a rich operating system of the mobile computing device different than a mobile operating system of the mobile computing device responsive to a request for a trusted user confirmation from a medication therapy application executed via the mobile operating system of the mobile device, the secure user interaction process comprising the trusted authentication service:

initiating a secure user interaction process:

using the secure interaction process:

prevent the mobile operating system from receiving, and allow the rich operating system to receive, a user input via a user interface of the mobile computing device;

while preventing the mobile operating system from receiving a user input via the user interface, present a request, via the user interface, for a trusted user confirmation of the user specified parameters; and responsive to receiving the trusted user confirmation, generating and providing the signature and success message to the medication therapy application.

17. The reusable insulin pen cap of claim 16, further comprising:

a read only memory (ROM) storing one or more public keys; and a signature authenticator configured to authenticate the signature using the one or more public keys.

18. An accessory that is associated with at least one insulin delivery device and is configured to receive user-specified parameters from a mobile computing device and use the user-specified parameters to make insulin therapy recommendations, wherein the accessory is configured to use the user-specified parameters responsive to a signature received from the mobile computing device, wherein the signature is indicative that the user-specified parameters were confirmed using a secure user interaction process at the mobile computing device, the secure user interaction process being initiated by a trusted authentication service that executes in a secure execution environment including a secure kernel configured to handle commands and access isolated hardware resources including a processor, memory and device I/O, the trusted authentication service executed via a rich operating system of the mobile computing device different than a mobile operating system of the mobile computing device responsive to a request for a trusted user confirmation from a medication therapy application executed via the mobile operating system of the mobile device, the secure user interaction process comprising the trusted authentication service:

initiating a secure user interaction process; and using the secure user interaction process:

prevent the mobile operating system from receiving, and allow the rich operating system to receive, a user input via a user interface of the mobile computing device;

while the mobile operating system is prevented from receiving a user input via the user interface, present a request, via the user interface, for a trusted user confirmation of the user specified parameters; and responsive to receiving the trusted user confirmation, generating and providing the signature and success message to the medication therapy application.

19. The mobile computing device of claim 1, wherein the secure execution environment is configured to execute on a separate processor, memory, or device I/O than the normal execution environment.

20. The mobile computing device of claim 19, wherein the secure execution environment further comprises a secure kernel in communication with the rich operating system and the separate processor, memory, or device I/O, wherein the secure kernel is configured to provide commands received from the rich operating system and provide the commands to the separate processor, memory, or device I/O.

* * * * *